United States Patent
Dikeman et al.

(10) Patent No.: US 8,052,648 B2
(45) Date of Patent: Nov. 8, 2011

(54) INTRAVENOUS CATHETER ANCHORING DEVICE

(75) Inventors: W. Cary Dikeman, Lenexa, KS (US); Chris Winsor, Olathe, KS (US); Steve A. Cash, Overland Park, KS (US); Larry C. Smith, Shawnee, KS (US)

(73) Assignee: Venetec International, Inc., Covington, GA (US)

( * ) Notice: Subject to any disclaimer, the term of this patent is extended or adjusted under 35 U.S.C. 154(b) by 1331 days.

(21) Appl. No.: 11/306,289

(22) Filed: Dec. 21, 2005

(65) Prior Publication Data

US 2007/0142784 A1 Jun. 21, 2007

(51) Int. Cl.
*A61M 5/32* (2006.01)
(52) U.S. Cl. ...................................................... 604/174
(58) Field of Classification Search ........... 604/174–180
See application file for complete search history.

(56) References Cited

U.S. PATENT DOCUMENTS

| | | | |
|---|---|---|---|
| 2,525,398 A | 10/1950 | Collins | |
| 2,553,961 A | 12/1950 | Rousseau et al. | |
| 2,707,953 A | 5/1955 | Ryan | |
| 3,059,645 A | 10/1962 | Hasbrouck et al. | |
| 3,064,648 A | 11/1962 | Bujan | |
| 3,167,072 A | 1/1965 | Stone et al. | |
| 3,204,636 A | 9/1965 | Kariher et al. | |
| 3,256,880 A | 6/1966 | Caypinar | |
| 3,289,671 A | 12/1966 | Troutman et al. | |
| 3,482,569 A | 12/1969 | Raaelli, Sr | |
| 3,524,443 A | 8/1970 | Batlin | |
| 3,529,597 A | 9/1970 | Fuzak | |
| 3,542,321 A | 11/1970 | Kahabka | |
| 3,602,227 A | 8/1971 | Andrew | |
| 3,630,195 A | 12/1971 | Santomieri | |
| 3,632,071 A | 1/1972 | Cameron et al. | |
| 3,677,250 A | 7/1972 | Thomas | |
| 3,766,915 A | 10/1973 | Rychlik | |
| 3,834,380 A | 9/1974 | Boyd | |
| 3,847,370 A | 11/1974 | Engelsher | |
| 3,856,020 A | 12/1974 | Kovac | |
| 3,896,527 A | 7/1975 | Miller et al. | |

(Continued)

FOREIGN PATENT DOCUMENTS

CA 995995 8/1976

(Continued)

OTHER PUBLICATIONS

"Occlude". Merriam-Webster Online Dictionary. <http://www.merriam-webster.com/dictionary/occlude>.*

(Continued)

*Primary Examiner* — Kevin C Sirmons
*Assistant Examiner* — Kami A Bosworth
(74) *Attorney, Agent, or Firm* — Knobbe Martens Olson & Bear LLP

(57) ABSTRACT

An intravenous catheter anchoring assembly is disclosed and includes a patient-contacting membrane, a platform, and a retaining strap for securing a catheter or tubing of an administration set to a patient. The strap is attached to the platform with adjustable pull-tabs that permit a variety of catheter shapes and sizes to be secured. The strap is also elastomeric so that the strap is stretchable and thereby grabs the secured catheter. The strap and platform further define a plurality of passageways that permit the catheter to be secured in a plurality of non-aligned directions.

94 Claims, 12 Drawing Sheets

U.S. PATENT DOCUMENTS

| | | |
|---|---|---|
| 3,900,026 A | 8/1975 | Wagner |
| 3,906,946 A | 9/1975 | Nordstrom |
| 3,942,228 A | 3/1976 | Buckman et al. |
| 3,942,750 A | 3/1976 | Noorily |
| 3,973,565 A | 8/1976 | Steer |
| 3,993,081 A | 11/1976 | Cussell |
| 4,020,835 A | 5/1977 | Nordstrom et al. |
| 4,030,540 A | 6/1977 | Roma |
| 4,057,066 A | 11/1977 | Taylor |
| 4,059,105 A | 11/1977 | Cutruzzula et al. |
| 4,082,094 A | 4/1978 | Dailey |
| 4,114,618 A | 9/1978 | Vargas |
| 4,114,626 A | 9/1978 | Beran |
| 4,129,128 A | 12/1978 | McFarlane |
| 4,133,307 A | 1/1979 | Ness |
| 4,142,527 A | 3/1979 | Garcia |
| 4,149,539 A | 4/1979 | Cianci |
| 4,161,177 A | 7/1979 | Fuchs |
| 4,170,995 A | 10/1979 | Levine et al. |
| 4,193,174 A | 3/1980 | Stephens |
| 4,224,937 A | 9/1980 | Gordon |
| 4,248,229 A | 2/1981 | Miller |
| 4,250,880 A | 2/1981 | Gordon |
| 4,316,461 A | 2/1982 | Marais et al. |
| 4,324,236 A | 4/1982 | Gordon et al. |
| 4,326,519 A | 4/1982 | D'Alo et al. |
| 4,353,369 A | 10/1982 | Muetterties et al. |
| 4,362,156 A | 12/1982 | Feller, Jr. et al. |
| 4,392,853 A | 7/1983 | Muto |
| 4,392,857 A | 7/1983 | Beran |
| 4,397,647 A | 8/1983 | Gordon |
| 4,442,994 A | 4/1984 | Logsdon |
| 4,449,975 A | 5/1984 | Perry |
| 4,453,933 A | 6/1984 | Speaker |
| 4,474,559 A | 10/1984 | Steiger |
| 4,480,639 A | 11/1984 | Peterson et al. |
| 4,484,913 A | 11/1984 | Swauger |
| 4,498,903 A | 2/1985 | Mathew |
| 4,516,293 A | 5/1985 | Beran |
| 4,516,968 A | 5/1985 | Marshall et al. |
| 4,517,971 A | 5/1985 | Sorbonne |
| 4,563,177 A | 1/1986 | Kamen |
| 4,617,017 A | 10/1986 | Hubbard et al. |
| 4,623,102 A | 11/1986 | Hough, Jr. |
| 4,633,863 A | 1/1987 | Filips et al. |
| 4,650,473 A | 3/1987 | Bartholomew et al. |
| 4,660,555 A | 4/1987 | Payton |
| 4,669,156 A | 6/1987 | Goido et al. |
| 4,711,636 A | 12/1987 | Bierman |
| D293,717 S | 1/1988 | Proulx et al. |
| 4,737,143 A | 4/1988 | Russell |
| 4,742,824 A | 5/1988 | Payton et al. |
| 4,762,513 A | 8/1988 | Choy et al. |
| 4,775,121 A | 10/1988 | Carty |
| 4,808,162 A | 2/1989 | Oliver |
| 4,823,789 A | 4/1989 | Beisang, III |
| 4,826,486 A | 5/1989 | Palsrok et al. |
| 4,828,549 A | 5/1989 | Kvalo |
| 4,852,844 A | 8/1989 | Villaveces |
| 4,857,058 A | 8/1989 | Payton |
| 4,863,432 A | 9/1989 | Kvalo |
| 4,869,465 A | 9/1989 | Yirmiyahu et al. |
| 4,880,412 A | 11/1989 | Weiss |
| 4,881,705 A | 11/1989 | Kraus |
| 4,896,465 A | 1/1990 | Rhodes et al. |
| 4,897,082 A | 1/1990 | Erskine |
| 4,898,587 A | 2/1990 | Mera |
| 4,899,963 A | 2/1990 | Murphy |
| 4,919,654 A | 4/1990 | Kalt |
| D308,576 S | 6/1990 | Iversen |
| 4,932,943 A | 6/1990 | Nowak |
| 4,944,728 A | 7/1990 | Carrell et al. |
| 4,952,207 A | 8/1990 | Lemieux |
| 4,955,864 A | 9/1990 | Hajduch |
| 4,976,700 A | 12/1990 | Tollini |
| 4,997,421 A | 3/1991 | Palsrok et al. |
| 5,000,741 A | 3/1991 | Kalt |
| 5,037,397 A | 8/1991 | Kalt et al. |
| 5,073,166 A | 12/1991 | Parks et al. |
| 5,073,170 A | 12/1991 | Schneider |
| 5,078,731 A | 1/1992 | Hayhurst |
| 5,084,026 A | 1/1992 | Shapiro |
| 5,098,399 A | 3/1992 | Tollini |
| 5,112,313 A | 5/1992 | Sallee |
| 5,147,322 A | 9/1992 | Bowen et al. |
| 5,156,641 A | 10/1992 | White |
| 5,163,914 A | 11/1992 | Abel |
| 5,192,273 A | 3/1993 | Bierman et al. |
| 5,192,274 A | 3/1993 | Bierman |
| 5,195,981 A | 3/1993 | Johnson |
| 5,226,892 A | 7/1993 | Boswell |
| 5,234,185 A | 8/1993 | Hoffman et al. |
| 5,257,768 A | 11/1993 | Juenemann et al. |
| 5,263,943 A | 11/1993 | Vanderbrook |
| 5,266,401 A | 11/1993 | Tollini |
| 5,267,967 A | 12/1993 | Schneider |
| 5,280,866 A | 1/1994 | Ueki |
| 5,282,463 A | 2/1994 | Hammersley |
| 5,290,248 A | 3/1994 | Bierman et al. |
| 5,292,312 A | 3/1994 | Delk et al. |
| 5,304,146 A | 4/1994 | Johnson et al. |
| 5,306,243 A | 4/1994 | Bonaldo |
| D347,060 S | 5/1994 | Bierman |
| 5,314,411 A | 5/1994 | Bierman et al. |
| 5,318,546 A | 6/1994 | Bierman |
| 5,322,514 A | 6/1994 | Steube et al. |
| 5,330,438 A | 7/1994 | Gollobin et al. |
| 5,334,186 A | 8/1994 | Alexander |
| 5,338,308 A | 8/1994 | Wilk |
| 5,342,317 A | 8/1994 | Claywell |
| 5,344,406 A | 9/1994 | Spooner |
| 5,344,414 A | 9/1994 | Lopez et al. |
| 5,346,479 A | 9/1994 | Schneider |
| 5,352,211 A | 10/1994 | Merskelly |
| 5,354,282 A | 10/1994 | Bierman |
| 5,354,283 A | 10/1994 | Bark et al. |
| 5,374,254 A | 12/1994 | Buma |
| 5,380,293 A | 1/1995 | Grant |
| 5,380,294 A | 1/1995 | Persson |
| 5,380,301 A | 1/1995 | Prichard et al. |
| 5,382,239 A | 1/1995 | Orr et al. |
| 5,382,240 A | 1/1995 | Lam |
| 5,389,082 A | 2/1995 | Baugues et al. |
| 5,395,344 A | 3/1995 | Beisang, III et al. |
| 5,397,639 A | 3/1995 | Tollini |
| 5,403,285 A | 4/1995 | Roberts |
| 5,413,562 A | 5/1995 | Swuager |
| 5,443,460 A | 8/1995 | Miklusek |
| 5,449,349 A | 9/1995 | Sallee et al. |
| 5,456,671 A | 10/1995 | Bierman |
| 5,468,228 A | 11/1995 | Gebert |
| 5,468,230 A | 11/1995 | Corn |
| 5,468,231 A | 11/1995 | Newman et al. |
| 5,470,321 A | 11/1995 | Forster et al. |
| D364,922 S | 12/1995 | Bierman |
| 5,474,572 A | 12/1995 | Hayhurst |
| 5,147,322 A | 1/1996 | Bowen et al. |
| 5,484,420 A | 1/1996 | Russo |
| 5,496,282 A | 3/1996 | Militzer et al. |
| 5,496,283 A | 3/1996 | Alexander |
| 5,499,976 A | 3/1996 | Dalton |
| 5,520,656 A | 5/1996 | Byrd |
| 5,522,803 A | 6/1996 | Teissen-Simony |
| 5,527,293 A | 6/1996 | Zamierowski |
| 5,549,567 A | 8/1996 | Wolman |
| D375,355 S | 11/1996 | Bierman |
| D375,356 S | 11/1996 | Bierman |
| 5,578,013 A | 11/1996 | Bierman |
| D377,831 S | 2/1997 | Bierman |
| 5,613,655 A | 3/1997 | Marion |
| 5,616,135 A | 4/1997 | Thorne et al. |
| 5,632,274 A | 5/1997 | Quedens |
| 5,637,098 A | 6/1997 | Bierman |
| 5,653,411 A | 8/1997 | Picco et al. |
| 5,693,032 A | 12/1997 | Bierman |
| 5,697,907 A | 12/1997 | Gaba |
| 5,702,371 A | 12/1997 | Bierman |

| | | |
|---|---|---|
| D389,911 S | 1/1998 | Bierman |
| 5,722,959 A | 3/1998 | Bierman |
| D393,903 S | 4/1998 | Bierman |
| 5,738,660 A | 4/1998 | Luther |
| 5,785,201 A | 7/1998 | Bordner et al. |
| 5,795,335 A | 8/1998 | Zinreich |
| 5,800,402 A | 9/1998 | Bierman |
| 5,810,781 A | 9/1998 | Bierman |
| D399,954 S | 10/1998 | Bierman |
| 5,827,230 A | 10/1998 | Bierman |
| D401,329 S | 11/1998 | Bierman |
| 5,833,663 A | 11/1998 | Bierman et al. |
| D404,815 S | 1/1999 | Bierman |
| 5,921,991 A | 7/1999 | Whitehead et al. |
| 5,941,263 A | 8/1999 | Bierman |
| 5,944,696 A | 8/1999 | Bayless et al. |
| 6,001,081 A | 12/1999 | Collen |
| 6,024,761 A | 2/2000 | Barone et al. |
| 6,027,480 A | 2/2000 | Davis et al. |
| D425,619 S | 5/2000 | Bierman |
| 6,117,163 A | 9/2000 | Bierman |
| 6,132,398 A | 10/2000 | Bierman |
| 6,213,979 B1 | 4/2001 | Bierman |
| 6,224,571 B1 | 5/2001 | Bierman |
| 6,274,786 B1 | 8/2001 | Heller |
| 6,283,945 B1 | 9/2001 | Bierman |
| 6,290,676 B1 | 9/2001 | Bierman |
| 6,332,874 B1 | 12/2001 | Eliasen et al. |
| 6,361,523 B1 | 3/2002 | Bierman |
| 6,413,240 B1 | 7/2002 | Bierman et al. |
| 6,428,515 B1 | 8/2002 | Bierman et al. |
| 6,447,485 B2 | 9/2002 | Bierman |
| 6,458,104 B2 | 10/2002 | Gautsche |
| 6,491,664 B2 | 12/2002 | Bierman |
| D470,936 S | 2/2003 | Bierman |
| 6,551,285 B1 | 4/2003 | Bierman |
| 6,572,588 B1 | 6/2003 | Bierman et al. |
| 6,582,403 B1 | 6/2003 | Bierman et al. |
| 6,585,703 B1 | 7/2003 | Kassel et al. |
| D480,144 S | 9/2003 | Adams et al. |
| 6,663,600 B2 | 12/2003 | Bierman et al. |
| 6,685,670 B2 | 2/2004 | Miles et al. |
| D492,411 S | 6/2004 | Bierman |
| 6,770,055 B2 | 8/2004 | Bierman et al. |
| 6,786,892 B2 | 9/2004 | Bierman |
| 6,796,310 B2 | 9/2004 | Bierman |
| 6,829,705 B2 | 12/2004 | Smith |
| 6,837,875 B1 | 1/2005 | Bierman |
| 6,872,194 B2 | 3/2005 | Doyle et al. |
| D503,977 S | 4/2005 | Bierman |
| 6,984,145 B1 | 1/2006 | Lim et al. |
| 7,320,681 B2 | 1/2008 | Gillis et al. |
| 7,354,421 B2 | 4/2008 | Bierman |
| 2002/0026152 A1 | 2/2002 | Bierman |
| 2002/0095119 A1 | 7/2002 | Bertoch et al. |
| 2003/0125668 A1 | 7/2003 | Bierman |
| 2004/0167475 A1 | 8/2004 | Wright et al. |
| 2005/0205708 A1 | 9/2005 | Sasaki et al. |

FOREIGN PATENT DOCUMENTS

| | | |
|---|---|---|
| CA | 2281457 | 2/2001 |
| DE | 2341297 | 8/1973 |
| DE | 4000380 | 1/1990 |
| DE | 29608294 | 8/1996 |
| EP | 0064284 | 4/1982 |
| EP | 0247590 | 12/1987 |
| EP | 0356683 | 7/1989 |
| EP | 0597213 | 5/1994 |
| FR | 1184139 | 7/1959 |
| FR | 2381529 | 9/1978 |
| FR | 2722414 | 7/1994 |
| FR | 2852520 | 3/2003 |
| GB | 2063679 | 6/1981 |
| GB | 2086466 | 5/1982 |
| GB | 2312619 | 10/1997 |
| JP | 199251767 | 3/1992 |
| JP | 06063153 | 3/1994 |
| JP | 199528563 | 1/1995 |
| JP | 08024344 | 1/1996 |
| WO | 80/01458 | 7/1980 |
| WO | 8502774 | 7/1985 |
| WO | 9116939 | 11/1991 |
| WO | 9219309 | 11/1992 |
| WO | 9610435 | 4/1996 |
| WO | 9626756 | 9/1996 |

OTHER PUBLICATIONS

Plaintiff's Opening Claim Construction Brief; *Venetec International Inc. v. Nexus Medical , LLC*, U.S. District Court for Delaware, Case No. 07-CV-0057, Oct. 10, 2008, 45 pgs.

Plantiff's Answering Brief in Opposition to Defendant's Motion for Summary Judgement of invalidity; Filed: Oct. 30, 2008; *Venetec International, Inc., v. Nexus Medical, LLC*; USDC, District of Delaware, Civil Action No. 07-cv-0057-MPT.

Rebuttal Expert Report of dr. Terry N. Layton, PH.D., *Venetec International Inc. v, Nexus Medical, LLC*, U.S. District Court for Delaware, Case No. 07-CV-0057, Aug. 29, 2008, 33 pgs.

Stipulation and Order amending Nexus Medical, LLC's Answer to Complaint and Counterclaim, *Venetec International Inc. v. Nexus Medical, LLC*, U.S. District Court for Delaware, Case No. 07-CV-0057, 15 pgs.

Transcript of Claim Construction Hearing; *Venetec International Inc. v. Nexus Medical, LLC*, U.S. District Court for Delaware. Case No. 07-CV-0057, Nov. 21, 2008, 70 pgs.

Venetec's letter to Judge Thynge dated Sep. 28, 2007, *Venetec International Inc. v. Nexus Medical, LLC*, U.S. District Court for Delaware, Case No. 07-CV-0057, 6 pgs.

Joint Claim Construction Chart; *Venetec International Inc. v. Nexus Medical, LLC*, U.S. District Court for Delaware, Case No. 07-CV-0057, Oct. 10, 2008, 91 pgs.

Judge Thynge's Order Denying Nexus Motion to Stay Proceedings Pending Reexamination, *Venetec International Inc. v. Nexus Medical, LLC*, U.S. District Court for Delaware, Case No. 07-CV 0057, 1 pg.

Memorandum Order; *Venetec International Inc. v. Nexus Medical, LLC*, U.S. District Court for Delaware, Case No. 07-CV-0057, Mar. 28, 2008, 16 pgs.

Nexus' letter to Judge Thynge dated Sep. 28, 2007, *Venetec International Inc. v. Nexus Medical, LLC*, U.S. District Court for Delaware, Case No. 07-CV-0057, 2 pgs.

Nexus Medical LLC's Opening Claim Construction Brief; *Venetec International Inc. v. Nexus Medical, LLC*, U.S. District Court for Delaware, Case No. 07-CV-0057, Oct. 10, 2008, 142 pgs.

Nexus Medical, LLC's Objections and Responses to Venetec International, Inc's First Set of Interrogatories, *Venetec International Inc. v. Nexus Medical, LLC*, U.S. District Court for Delaware Case No. 07-CV-0057, pp. 1-47.

Complaint [dated Jan. 29, 2007]. *Venetec Int'l, Inc. v. Nexus Medical, LLC*, USDC D.Del., Case No. 1:07-CV-00057.

Nexus Medical, LLC's Answer to Venetec International, Inc.'s Complaint and Counterclaim [dated Mar. 22, 2007]. *Venetec Int'l, Inc. v. Nexus Medical, LLC*, USDC D.Del., Case No. 1:07-CV-00057.

Venetec International, Inc.'s Reply to Nexus Medical, LLC's Counterclaim [filed Apr. 11, 2007]. *Venetec Int'l, Inc. v. Nexus Medical, LLC*, USDC D.Del., Case No. 1:07-CV-00057.

First Supplemental Complaint [dated Jul. 24, 2007]. *Venetec Int'l, Inc. v. Nexus Medical, LLC*, USDC D.Del., Case No. 1:07-CV-00057.

Nexus Medical, LLC's Answer to Venetec International, Inc.'s First Supplemental Complaint and Counterclaim [dated Aug. 8, 2007]. *Venetec Int'l, Inc. v. Nexus Medical, LLC*, USDC D.Del., Case No. 1:07-CV-00057.

Venetec International, Inc.'s Reply to Nexus Medical, LLC's Counterclaim [filed Aug. 28, 2007]. *Venetec Int'l, Inc. v. Nexus Medical, LLC*, USDC D.Del., Case No. 1:07-CV-00057.

Second Supplemental Complaint [filed Sep. 5, 2007]. *Venetec Int'l, Inc. v. Nexus Medical, LLC*, USDC D.Del., Case No. 1:07-CV-00057.

Nexus Medical, LLC's Answer to Venetec International, Inc.'s Second Supplemental Complaint and Counterclaim [filed Sep. 19, 2007]. *Venetec Int'l, Inc. v. Nexus Medical, LLC*, USDC D.Del., Case No. 1:07-CV-00057.

Venetec International, Inc.'s Reply to Nexus Medical, LLC's Counterclaim [filed Sep. 27, 2007]. *Venetec Int'l, Inc. v. Nexus Medical, LLC*, USDC D.Del., Case No. 1:07-CV-00057.
Request for Inter Partes Reexamination Under 37 C.F.R. 1.913 [filed Jun. 25, 2007]. In re Bierman, USPTO, Reexamination No. 95/000,271.
Civil Docket for Case No. 1:07-CV-00057 [printed Oct. 22, 2007].
Brief in Support of Nexus Medical, LLC's Motion for Summary Judgement of Noninfringement of the Venetec Patents (Public Redacted Version); *Venetec International Inc. v. Nexus Medical, LLC*, U.S. District Court for Delaware, Case No. 07-CV-0057, Public version filed Oct. 24, 2008, 158 pgs.
Brief in Support of Nexus Medical, LLC's Motion for Summary Judgement that the Venetec Patents are Invalid; Filed Oct. 10, 2008; *Venetec International Inc. v. Nexus Medical, LLC*, USDC, District of Delaware, Civil Action No. 07-cv-0057-MPT.
Declaration of Jennifer C. Bailey in Support of Nexus' Opposition to Venetec's Motion for Partial Judgement on the Pleadings, *Venetec International Inc. v. Nexus Medical, LLC*, U.S. District Court for Delaware, Case No. 07-CV-0057, 31 pgs.
Defendant Nexus Medical, LLC's Reply to Plaintiff's Answering Brief in Opposition to Defendant's Motion for Summary Judgement of Invalidity; Filed: Nov. 10, 2008; *Venetec International Inc. v. Nexus Medical, LLC*; USDC, District of Delaware, Civil ActionNo. 07-cv-0057-MPT.
Defendant Nexus Medical, LLC's Reply to Plaintiff's Answering Brief in Opposition to Defendant's Motion for Summary Judgement of Noninfringement of the Venetec Patents (Public Version); *Venetec International Inc. v. Nexus Medical, LLC*, U.S. District Court for Delaware, Case No. 07-CV-0057, Public version filed Nov. 18, 2008, 27 pgs.
Expert Report of Julie E. Shomo Regarding Invalidity of the Venetec Patents Pursuant to Rule 26(a)(2)(B), *Venetec International Inc. v. Nexus Medical, LLC*, U.S. District Court for Delaware, Case No. 07-CV-0057, Jul. 18, 2008, 31 pgs.
Expert Report of Marvin Gordon Regarding Invalidity of the Venetec Patents Pursuant to Rule 26(a)(2)(B), *Venetec International Inc. v. Nexus Medical, LLC*, U.S. District Court for Delaware, Case No. 07-CV-0057, Jul. 18, 2008, 23 pgs.
Expert Report of William H. Hirsch Regarding Invalidity of the Venetec Patents Pursuant to Rule 26(a)(2)(B), *Venetec International Inc. v. Nexus Medical, LLC*, U.S. District Court for Delaware. Case No. 07-CV-0057, Jul. 18. 2008, 39 pgs.
Zefon International printout from www.zefon.com/medical/griplok. htm depicting prior art GRIP-LOK Universal Tubing Securement Device (printed Jun. 20, 2005).
Tri-State Hospital Supply Corporation, Centurion Healthcare Products brochure for LineGuard J-Loop Securement Device (Nov. 2, 2004).
Tri-State Hospital Supply Corporation, Centurion Healthcare Products brochure for SorbaView 2000 Window Dressing (Apr. 14, 2004).
Tri-State Hospital Supply Corporation, Centurion Healthcare Products brochure for IV Start Kits (Sep. 14, 2004).
Tri-State Hospital Supply Corporation, Centurion Healthcare Products brochure for HubGuard Catheter Securement (Mar. 3, 2004).
Tri-State Hospital Supply Corporation, Centurion Healthcare Products brochure for SorbaView Ultimate Window Dressing (May 7, 2004 and Jun. 22, 2004).
Tri-State Hospital Supply Corporation, Centurion Healthcare Products brochure for Port Access Trays (Apr. 24, 2003).
Venetec's Motion for Partial Judgement on the Pleadings, *Venetec International Inc. v. Nexus Medical, LLC*, U.S. District Court for Delaware, Case No. 07-CV-0057, 3 pgs.
Venetec's Opening Brief in Support of Motion for Partial Judgement on the Pleadings, *Venetec International Inc. v. Nexus Medical, LLC*, U.S. District Court for Delaware, Case No. 07-Cv-0057, 34 pgs.
Interview Summary in the Ex Parte Reexamination of the '979 patent, U.S. Appl. No. 90/010,167, mailed Dec. 19, 2008, 4 pgs.

Office Action issued to Venetec in the Ex Parte Reexamination of the '979 patent, U.S. Appl. No. 90/010,167, mailed Nov. 7, 2008, 21 pgs.
Patent Owner's Response to Office Action issued to Venetec in the Ex Parte Reexamination of the '979 patent, U.S. Appl. No. 90/010,167, Jan. 7, 2009, 42 pgs.
Defendant Nexus Medical, LLC's Objections and Responses to Plantiff Venetec International, Inc's Modified and Supplemental Definitions Set Forth in its First Set of interrogatories to Defendant Nexus Medical, LLC, *Venetec International Inc. v. Nexus Medical, LLC*, U.S. District Court for Delaware, Case No. 07-Cv-0057, 79 pgs.
Nexus' Opposition to Venetec's Motion for Partial Judgement on the Pleadings, *Venetec International Inc. v. Nexus Medical, LLC*, U.S. District Court for Delaware, Case No. 07-CV-0057, 28 pgs.
Notice of Assignment of Inter Partes Reexamination Request for the '485 patent, *Venetec International Inc. v. Mexus Medical, LLC*, U,S. District Court for Delaware,Case No. 07-CV-0057 1 pg.
Notice of Assignment of Reexamination, U.S. Appl. No. 90/010,211, mailed Jul. 7, 2008, 1 pg.
Notice of Reexamination Request Filing Date, U.S. Appl. No. 90/010,211, mailed Jul. 7, 2008, 1 pg.
Office Action issued to Venetec in the Inter Partes Reexamination, *Venetec International Inc. v. Nexus Medical, LLC*, U.S. District Court for Delaware, Case No. 07-CV-0057, 23 pgs.
Order Granting Inter Partes Reexamination, *Venetec International Inc. v. Nexus Medical, LLC*, U.S. District Court for Delaware, Case No. 07-CV-0057, 29 pgs.
Order Granting Request for Ex Parte Reexamination of the '150 patent, U.S. Appl. No. 90/010,211, mailed Jul. 29, 2008, 16 pgs.
Patent Owner's Response to Office Action issued to Venetec in the Ex Parte Reexamination of the '150 patent, U.S. Appl. No. 90/010,211, Jan. 7, 2009, 36 pgs.
3M Technical Data Sheet enteitled "Adhesive Transfer Tapes with Ashesive 300MP 9692-9695-964" (Sep. 2002).
Bostick Findley Product Data Sheet entitled "4229 Hot Melt Adhesives" (Sep. 2003).
Hi-Tech Products Material Data Sheet entitled "Tricot PSA" (printed prior to Jul. 13, 2006).
Patent Owner's Supplemental Response to Office Action, Inter Partes Reexamination No. 95/000271, Sep. 29, 2008, 46 pgs.
Order Granting Request for Inter Partes Reexamination & Reexamination Non-Final Office Action, Inter Partes Reexamination No. 95/000271, Sep. 21, 2007, 50 pgs.
Order Granting Request for Ex Partes Reexamination, Ex Parte Reexamination of the '979 patent, U.S. Appl. No. 90/010,167, Jul. 29, 2008, 14 pgs.
Office Action in the Ex Parte Reexamination of the '150 patent, U.S. Appl. No. 90/010,211, dated May 11, 2009.
Office Action in the Ex Parte Reexamination of the '979 patent, U.S. Appl. No. 90/010,167, dated May 8, 2009.
Nexus Medical , LLC's First Amended Answer and Counterclaim to Venetec International, Inc.'s Second Supplemental Complaint and Counterclaim; *Venetec International Inc. v. Nexus Medical, LLC*, U.S. District Court for Delaware, Case No. 07-CV-0057, 50 pgs.
Patent Owner's Response to Office Action, Inter Partes Reexamination No. 95/000271, Nov. 21, 2007, 90 pgs.
Patent Owner's Supplemental Response to Office Action, Inter Partes Reexamination No. 95/000271, Dec. 21, 2007, 46 pgs.
Third-Party Requester's Response to Patent Owner's Response to Office Action Dated Sep. 21, 2007, Inter Partes Reexamination No. 95/000271, Dec. 21, 2007, 85 pages.
Third-Party Requester's Supplemental Response to Patent Owner's Supplemental Response to Office Action Dated Sep. 21, 2007, Inter Partes Reexamination No. 95/000271, Jan. 22, 2008, 48 pgs.
Interview Summary in the Ex Parte Reexamination of the '150 patent, U.S. Appl. No. 90/010,211, mailed Dec. 19, 2008, 3 pgs.
Office Action issued to Venetec in the Ex Parte Reexamination of the '150 patent, U.S. Appl. No. 90/010,211, mailed Nov. 7, 2008, 20 pgs.

\* cited by examiner

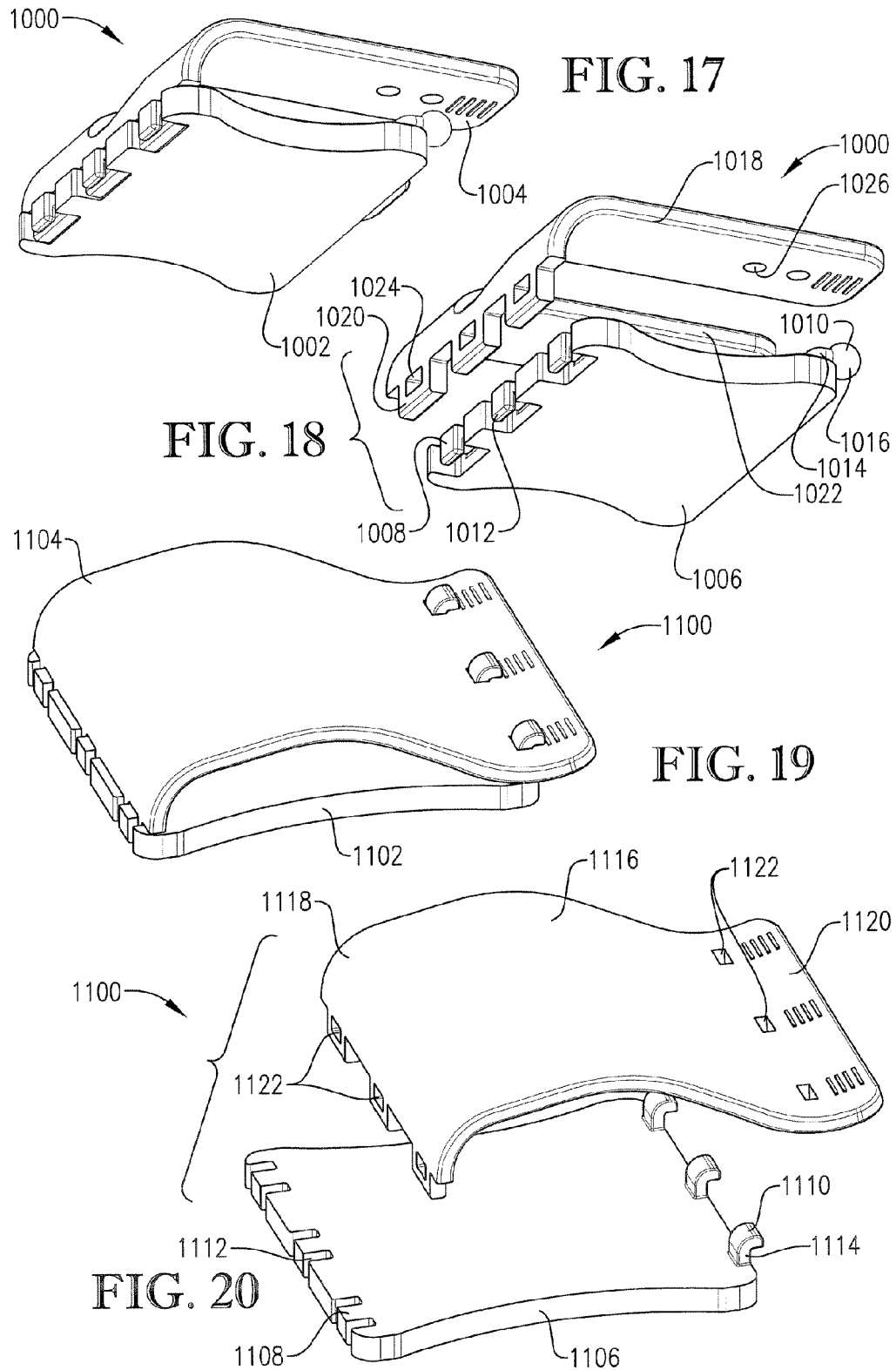

INTRAVENOUS CATHETER ANCHORING DEVICE

CROSS REFERENCE TO RELATED APPLICATION

This application is being filed contemporaneously with application for U.S. Design patent Ser. No. 29/245,311, entitled INTRAVENOUS SITE SECUREMENT DEVICE FOR CATHETERS, which is hereby incorporated by reference herein.

BACKGROUND OF THE INVENTION

1. Field of the Invention

The present invention relates generally to the field of intravenous infusion site devices. More specifically, the present invention concerns an intravenous catheter anchoring device for the securement of catheters on various patient sites.

2. Discussion of Prior Art

Catheters for intravenous infusion into a patient are well known in the art. Such catheters are generally used in a variety of infusion applications and on a variety of sites. For example, catheters are commonly used as central venous catheters (CVC), midline catheters, or peripherally inserted central catheters (PICC). These catheters normally are used with some sort of a catheter anchoring device for attaching the catheter to the patient.

One such anchoring device is an intravenous site securement device for preventing catheter movement. The securement device is important because catheter location within the venous system is usually critical. For example, a catheter that dispenses medicine to an internal organ often must have its tip positioned in a particular location or the medicine will not have its intended effect. Moreover, patients with these catheters often want or need to have a normal range of body motion while the catheter is inserted. Patient movement as well as external objects can apply external forces to the catheter and thereby shift the catheter's location within the venous system. These forces can cause, in particular, back-and-forth dynamic movement of the tip, sometimes referred to as pistoning. These forces can also cause a static shift in the catheter tip from its original location.

Another type of catheter anchoring device is a tubing collector. The tubing collector generally serves to secure an excess length of tubing from a catheter, intravenous extension set, or intravenous administration set. Also, some tubing collectors tend to permit axial movement of the secured tubing. Therefore, people have a need for catheter anchoring devices that provide reliable catheter securement during patient movement or while an external force is applied.

Again, anchoring devices are often used with catheters to prevent or restrict catheter movement. However, these anchoring devices are problematic and suffer from various undesirable limitations. One limitation for site securement devices with tape or sutures holding the catheter in place is that they tend to start or promote infections at that location. Furthermore, these securement devices often are able to receive only one size and shape of catheter hub (e.g., a suture hub, Y-site hub, or luer fitting). One limitation for anchoring devices in general is that catheter attachment is difficult, requiring precise, two-handed manipulation. Anchoring devices are also problematic because they can be inadvertently pulled from the skin's surface. Another limitation is that anchoring devices are not adapted for use with a variety of catheter sizes and shapes. Accordingly, there is a need for an improved intravenous catheter anchoring device that does not suffer from these problems and limitations.

SUMMARY OF THE INVENTION

The present invention provides an intravenous catheter anchoring device that does not suffer from the problems and limitations of the prior art catheter anchoring devices detailed above.

In particular, a first aspect of the present invention concerns an intravenous catheter anchoring device for securing a catheter to a patient, wherein the catheter includes a distal section configured to be at least partially inserted into the patient and a proximal section. The device broadly includes a platform configured for removable attachment to the patient and a retaining strap. The retaining strap cooperates with the platform to define a catheter-receiving passageway that is configured to receive a portion of the catheter with the proximal and distal sections projecting outwardly therefrom. The retaining strap comprises an elastomeric body. The body is elastically stretched when the catheter portion is received in the passageway such that the catheter is gripped and thereby axially retained by the device.

A second aspect of the present invention concerns an intravenous catheter anchoring device for securing a catheter to a patient, wherein the catheter includes a distal section configured to be at least partially inserted into the patient and a proximal section. The device broadly includes a platform configured for removable attachment to the patient and a retaining strap. The platform presents a connector. The retaining strap cooperates with the platform to define a catheter-receiving passageway configured to receive a portion of the catheter with the proximal and distal sections projecting outwardly therefrom. The retaining strap comprises an elongated flexible body presenting spaced apart opposite ends, one of which is coupled to the platform and the other which is removably attached to the connector. The body includes a plurality of discrete attachment locations spaced along the length of the body, with each of the attachment locations being releasably connectable to the connector. The catheter-receiving passageway presents an adjustable cross-sectional dimension that varies depending upon which attachment location is connected to the connector.

A third aspect of the present invention concerns an intravenous catheter anchoring device for securing a catheter to a patient, wherein the catheter includes a distal section configured to be at least partially inserted into the patient and a proximal section. The device broadly includes a platform configured for removable attachment to the patient and a retaining strap. The retaining strap cooperates with the platform to define a plurality of non-aligned catheter-receiving passageways, each being configured to receive a portion of the catheter with the proximal and distal sections projecting outwardly therefrom. The passageways cooperatively provide multiple catheter orientations relative to the device. The platform and strap are intercoupled at more than two coupling locations. The platform and strap cooperatively define a plurality of catheter-receiving openings, each of which is between adjacent ones of the coupling locations. Each of the passageways extends between a corresponding pair of catheter-receiving openings.

A fourth aspect of the present invention concerns a method of securing a catheter to a patient. The method broadly includes the steps of attaching an intravenous catheter anchoring device to the patient, and attaching the catheter to the intravenous catheter anchoring device so as to restrict axial movement of the catheter relative to the device. The step of attaching the catheter to the anchoring devices includes the step of gripping the catheter with an elastically stretched retaining strap of the catheter anchoring device.

Other aspects and advantages of the present invention will be apparent from the following detailed description of the preferred embodiments and the accompanying drawing figures.

BRIEF DESCRIPTION OF THE DRAWING FIGURES

Preferred embodiments of the invention are described in detail below with reference to the attached drawing figures, wherein:

FIG. 17 is a perspective view of a tenth embodiment of the intravenous catheter anchoring assembly, showing a seventh alternative retaining strap and a fourth alternative platform that cooperatively form an alternative hinged connection and where the platform includes first alternative connectors;

FIG. 18 is an exploded perspective view of the intravenous catheter anchoring assembly shown in FIG. 17;

FIG. 19 is a perspective view of an eleventh embodiment of the intravenous catheter anchoring assembly, showing an eighth alternative retaining strap and a fifth alternative platform that cooperatively form an alternative hinged connection and where the platform includes second alternative connectors;

FIG. 20 is an exploded perspective view of the intravenous catheter anchoring assembly shown in FIG. 19;

Figure 1:
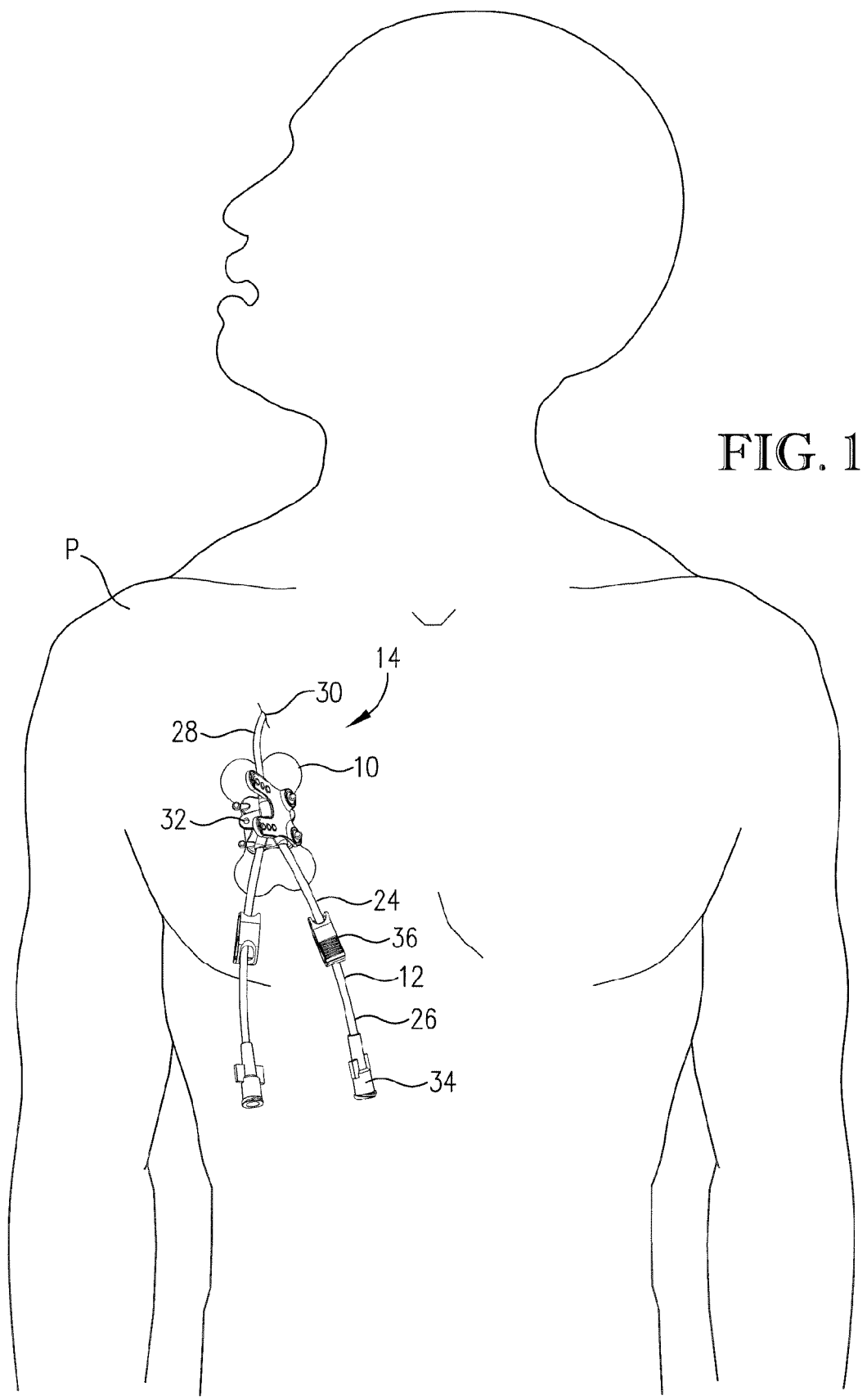
FIG. 1 is a perspective view of an intravenous infusion site assembly including an intravenous catheter anchoring assembly constructed in accordance with a preferred embodiment of the present invention, particularly showing the anchoring assembly as it secures a multi-lumen catheter with a Y-site suture hub of a central venous catheter to a patient.

The drawing figures do not limit the present invention to the specific embodiments disclosed and described herein. The drawings are not necessarily to scale, emphasis instead being placed upon clearly illustrating the principles of the invention.

DETAILED DESCRIPTION OF THE PREFERRED EMBODIMENTS

An intravenous catheter anchoring assembly 10 for use in securing a catheter 12 to a patient P is illustrated in FIG. 1. The catheter anchoring assembly 10 is combined with the catheter 12 to form an intravenous infusion site assembly 14. In the usual manner, the infusion site assembly 14 is connected to an intravenous administration set (not shown) and enables convenient and repetitive porting to the patient's internal venous system for intravenous therapy and generally for introducing or removing fluids. More specifically, the illustrated catheter anchoring assembly 10 functions as an intravenous site securement device for removably attaching the catheter 12 to the patient P to prevent localized catheter movement, especially any axial catheter movement, i.e., "pistoning".

As will be shown, other catheter anchoring embodiments disclosed herein function primarily as a tubing collector. As previously discussed, tubing collectors generally permit removable attachment of the tubing of a catheter, an intravenous extension set, or of an intravenous administration set to the patient P and principally serve to store an excess length of that tubing (see FIG. 21).

Figure 2:
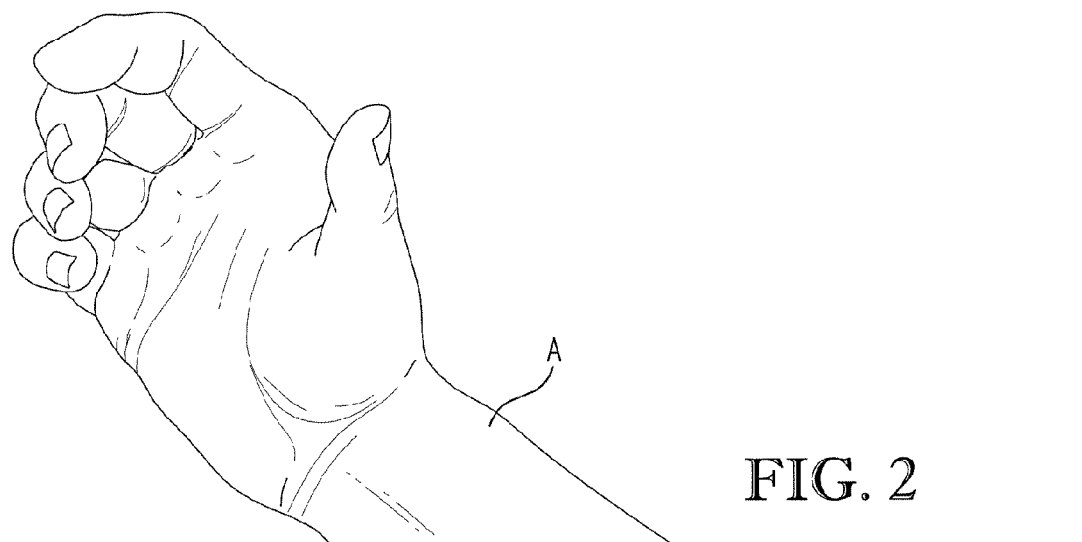
FIG. 2 is a perspective view of the intravenous catheter anchoring assembly depicted in FIG. 1, but showing the assembly as it secures a single-lumen catheter with a suture hub of a peripherally inserted central catheter to the patient's arm.

The illustrated embodiment of FIG. 1 specifically shows the infusion site assembly 14 with the catheter 12 secured to the patient's chest C as a CVC. However, the catheter 12 may be introduced into a fluid stream other than the blood stream without departing from the scope of the present invention. In particular, the illustrated catheter anchoring assembly 10 provides an external mechanism for stabilizing the catheter's position in various locations on the patient P. For example, FIG. 2 illustrates the catheter anchoring assembly 10 used to secure a catheter 16 on an arm A of the patient P as a PICC. In either case, the illustrated catheter anchoring assembly 10 broadly includes a patient-contacting membrane 18, a platform 20 adhesively attached to the membrane 18, and a retaining strap 22 removably attached to the platform 20. As discussed, the catheters 12,16 permit fluids to be introduced and removed from the patient's venous system.

The catheter 12 includes tubing 24 having an internal bore (not shown) that is also referred to as a lumen. The catheter 12 further includes proximal and distal sections 26,28 (with "proximal" and "distal" referring to the relative proximity to the intravenous administration set). The distal section 28 extends into and out of the patient's body at a puncture location 30 (sometimes referred to as a venipuncture site). The distal section 28 also terminates at a Y-site suture hub 32. The proximal sections 26 terminate at the suture hub 32 and at ends 34 which are formed by female luer fittings. The proximal sections 26 of the CVC catheter 12 each include a single lumen, making the catheter 12 a double lumen catheter. The lumens are configured in the usual manner to carry fluids to and from the patient P. The catheter 12 also includes clamps 36 that occlude the tubing 24 by sealing the lumen and thereby prevent the flow of fluid from one end to the other.

The single lumen catheter 16, as shown in FIGS. 2-6, includes proximal and distal sections 38,40. The catheter 16 further includes tubing 42 with a single lumen 44 that extends into and out of the patient's arm A and is configured in the usual manner to carry fluids to and from the patient P. The catheter 16 further includes a suture hub 46 with the tubing 42 extending outwardly therefrom. As shown particularly in FIG. 6, the suture hub 46 includes a body 48 and oppositely extending wing-shaped projections 50. The projections 50 each include a hole 52 for securing the suture hub 46 with a suture. The body 48 is cylindrically shaped and includes tapered strain relief sections 54 that restrict some bending of the tubing 42 adjacent to the projections 50. The body 48 further includes an annular groove 56 (sometimes referred to as a suture groove).

Figure 25:
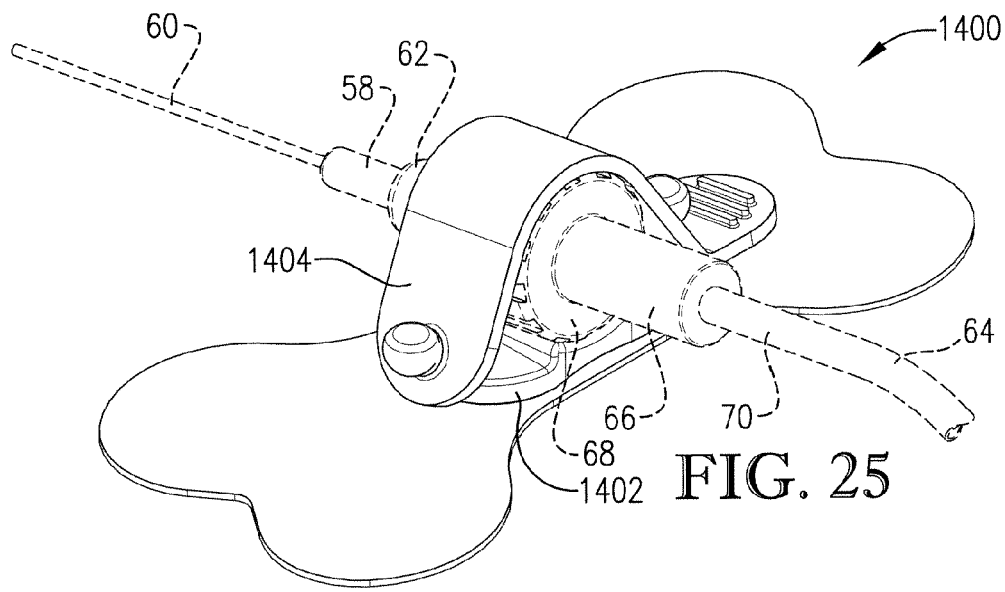
FIG. 25 is a perspective view of a fourteenth embodiment of the intravenous catheter anchoring assembly, which comprises a site securement device for securing an alternative catheter.

As shown in FIG. 25, another single lumen catheter 58 includes a distal tubing section 60 which, again carries fluids to and from the patient (not shown). The catheter 58 further includes a female luer fitting 62 which mates to an intravenous administration set 64. The intravenous administration set 64 includes a male luer fitting 66 for mating with the female fitting 62. These fittings 62,66 form a separable catheter hub 68. The intravenous administration set 64 further includes a proximal tubing section 70 that terminates at the male fitting 66. While the above described catheters 12,16,58 include features that are important with respect to some aspects of the invention, it is entirely consistent with the principles of the present invention to use other types of catheters not depicted with the disclosed embodiments of the catheter anchoring assembly. Moreover, the present invention is ideally and advantageously suited for securing a broad range of catheter shapes and sizes.

Turning back to FIGS. 3-6, the patient-contacting membrane 18 is preferably an adhesive strip that includes a substrate 72. Referring to FIG. 6, the substrate 72 includes ends 74 and recessed sides 76 extending longitudinally between the ends 74. The ends 74 each include two extended portions 78 and recessed scallops 80 between the pair of extended portions 78. The shape of the illustrated membrane 18 is intended for ornamental purposes and is the subject of co-pending U.S. Design Patent Application No. 29/253,412, filed Feb. 6, 2006, entitled ADHESIVE PATIENT-CONTACT STRIP FOR INTRAVENOUS CATHETER ANCHORING DEVICES, which is hereby incorporated by reference herein. The illustrated substrate 72 is a flexible, non-woven tricot fabric preferably including polyester filaments. However, it is consistent with the principles of the present invention to use other woven or non-woven fabrics.

The membrane 18 further includes a first adhesive layer 82 (see FIG. 2) coated over a lower side 84 of the substrate 72. The adhesive layer 82 is preferably a pressure-sensitive adhesive (PSA) including an acrylic resin material and is suitable for adhering itself to the substrate 72 as well as being removably adherent to human skin. More preferably, the adhesive layer 82 is provided with the substrate 72 as a pre-assembled adhesive-backed membrane. One preferred adhesive-backed membrane is Tricot PSA, sold by Hi-Tech Products, 8530 Roland St., Buena Park, Calif. 90621. The substrate 72 and adhesive layer 82 cooperatively permit the membrane 18 to be flexible and breathable and is thereby suitable for removable attachment to the skin of patient P. The membrane 18 includes a removable release layer (not shown) with tabs. The release layer covers the adhesive layer 82 and the tabs permit the release layer to be easily removable from the adhesive layer 82. In this manner, the adhesive layer 82 may be exposed just prior to adhering the membrane 18 to the patient's skin.

Turning to FIG. 6, a second adhesive layer 86 is applied to an upper side 88 of the substrate 72. The adhesive layer 86 is preferably an adhesive transfer tape that is suited for bonding fabrics or textured surfaces. More preferably, the adhesive layer 86 is an acrylic adhesive transfer tape, Type 964, manufactured by 3M, Engineered Adhesives Division, St. Paul, Minn. 55144-1000. The adhesive layer 86 is a flexible but solid material that is cut to closely follow the shape of the platform 20 in order to maximize the bonded surface area between the platform 20 and the substrate 72. However, it is consistent with the principles of the present invention that the adhesive layer 86 could be applied in a form more similar to a liquid and could be applied by pouring or spraying methods known to those of ordinary skill in the art. The adhesive layers 82,86 and their interaction with the platform 20 and the membrane 18 are the subject of co-pending U.S. patent application Ser. No. 11/457,279, filed Jul. 6, 2006, entitled INTRAVENOUS SECUREMENT DEVICE WITH ADHESIVELY INTERCONNECTED ANCHORING COMPONENT AND PERMEABLE ADHESIVE STRIP, which is hereby incorporated by reference herein.

Referring to FIGS. 3-7, the preferred platform 20 is unitary and includes a base 90 and connectors 92. The base 90 is shaped like a flat plate and includes upper and lower surfaces 94,96 and a contoured edge 98 (see FIG. 5). The contoured edge 98 is formed with rounded corners 100 and recessed scallops 102 between each of the corners 100 (see FIG. 6). The upper and lower surfaces 94,96 are substantially flat and give the base 90 a uniform thickness. However, as will be discussed in other embodiments, the base 90 can include alternatively shaped surfaces for receiving the catheter 16 without departing from the principles of the present invention. The base 90 could further have an alternative surface that is shaped to closely match the shape of the catheter 16, including the catheter hub 46.

The connectors 92 each include a post 104 having a rounded head end 106. As shown particularly in FIG. 5, the head end 106 is preferably frusto-spherical in shape, with a spherical portion and a flat 108. Also, the head end 106 is larger in diameter than the post 104. Referring back to FIG. 6, each of the posts 104 have a proximal end opposite from the head end 106 that is attached adjacent a respective corner 100 of the base 90. The posts 104 include two pairs that diverge upwardly from the upper surface 94 so that the head ends 106 are spaced apart further than the proximal ends.

The connectors 92 also form primary and secondary attachment sides 110,112. A first pair of the connectors 92 extend parallel to each other in a first lateral direction and are similarly angled relative to the base 90 so that they cooperatively define a primary attachment side 110 of the platform 20. A second pair of the connectors 92 also extend parallel to each other and cooperatively form another primary attachment side 110. The second pair are also angled relative to the base 90 at an angle similar to the first pair, but extend in an opposite lateral direction from the first pair. Each of the connectors 92 are spaced apart so that the distance between any two adjacent connectors 92 is about the same (thus forming the corners of an imaginary square). Therefore, adjacent connectors 92 that extend in opposite lateral directions from each other cooperatively form secondary attachment sides 112 of the platform 20.

In the preferred embodiment, the connectors 92 and base 90 are integrally injection molded of a relatively hard plastic to create the unitary platform 20. Alternatively, the platform 20 can be molded to include a relatively flexible elastomeric insert material (e.g., silicone). Elastomeric materials generally have a lower modulus of elasticity than hard plastic materials and also provide surfaces with a higher coefficient of friction. Therefore, such a material can be incorporated into the platform 20 so that the platform 20 has a surface that grips the catheter 16. Specifically, the elastomeric structure grips the catheter 16 by frictionally engaging and by flexibly conforming to the catheter 16.

While the use of elastomeric materials, such as silicone, is preferred for enabling the intravenous catheter anchoring assembly 10 to frictionally engage the catheter 16, for other aspects of the invention, it is also preferred to treat portions of the elastomer surface so that it is soft and has a relatively low coefficient of friction. In particular, for surfaces that come into contact with the patient's skin, the relatively sticky feel of silicone can be uncomfortable for the patient. One preferred solution is the application of a Parylene coating to the silicone (or other substrate) using a vapor deposition process. The process creates a uniform polymer film over the substrate that has a relatively soft feel against the patient's skin and is relatively slick. While the Parylene coating is not preferred for the catheter-gripping surfaces of the illustrated platform 20, other surfaces could include Parylene, particularly where those surfaces come into direct contact with the patient P.

Referring again to FIG. 6, the platform 20 is arranged so that the sides 110 are spaced adjacent to respective recessed sides 76 of the membrane 18. The platform 20 is bonded to the substrate 72 of membrane 18 with the adhesive layer 86. In particular, the adhesive layer 86 is bonded to the lower surface 96 and the upper side 88 of the substrate 72. Again, the features of the adhesive layer are further disclosed in the above incorporated Application. While the platform 20 is preferably adhered to the membrane 18, it is also within the ambit of the present invention that the platform 20 could be attached to the membrane 18 by other suitable manufacturing methods such as RF welding, ultrasonic welding, heat staking, or overmolding.

The combined platform 20 and membrane 18 are removably attachable to the patient's skin as discussed above. The membrane 18 flexes to conform to curved surfaces in the attachment site. Furthermore, the contoured shape of the relatively rigid platform 20 permits the platform 20 to remain bonded to the membrane 18 while being closely arranged to the patient's skin even if it includes significant curvature.

Turning back to FIGS. 3-7, the catheter anchoring assembly 10 includes the retaining strap 22. The preferred retaining strap 22 is unitary and is generally elongated and flat, although other suitable shapes and configurations are within the ambit of the present invention. As will be discussed in greater detail, the retaining strap 22 is also preferably flexible and elastomeric (see FIG. 3) to permit frictional engagement with the catheter 16 and to conform to the shape of the catheter 16.

Figure 6:
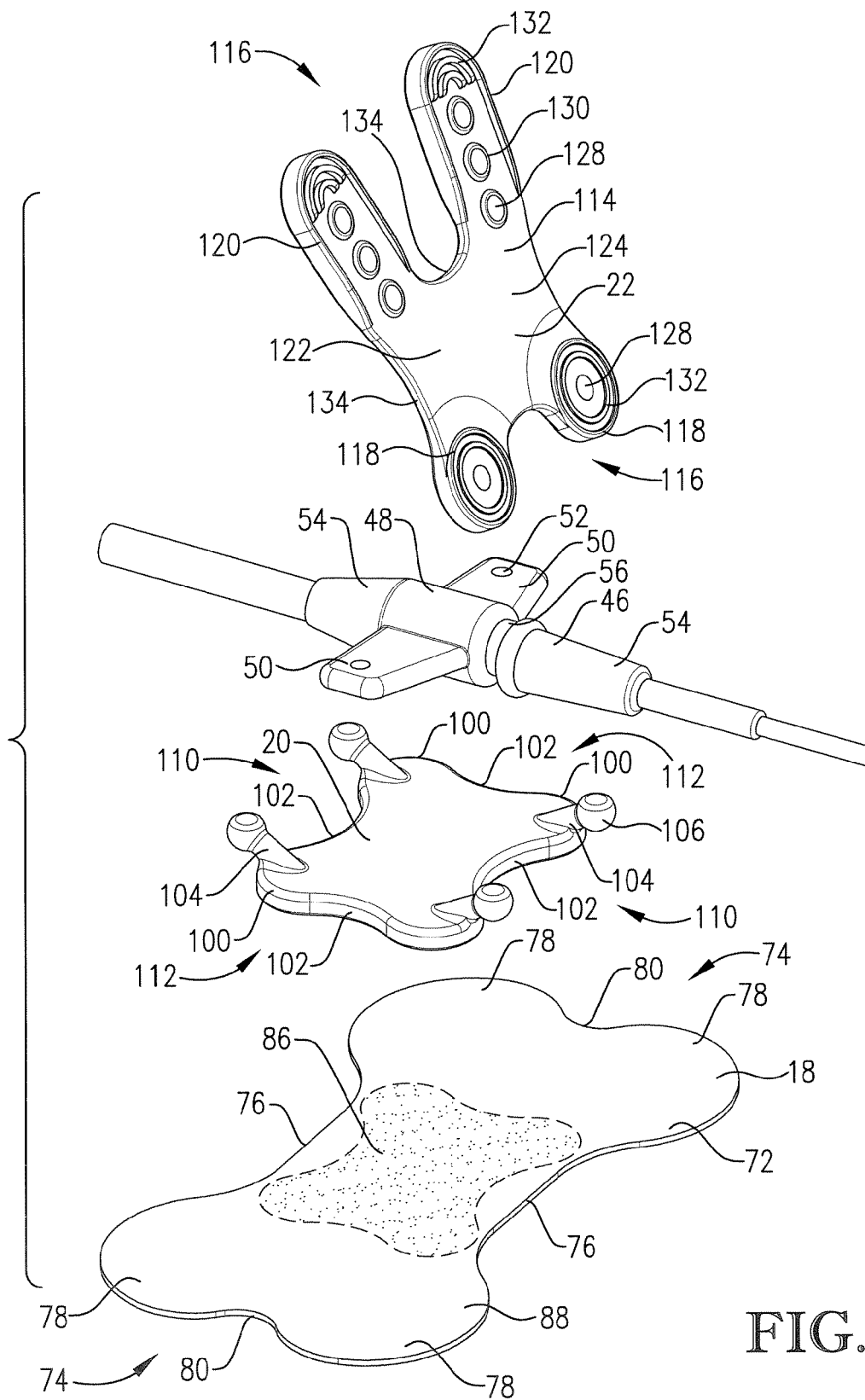
FIG. 6 is an exploded perspective view of the intravenous infusion site assembly shown in FIG. 3, particularly illustrating the patient-contact membrane, the platform, and the retaining strap.
Figure 7:
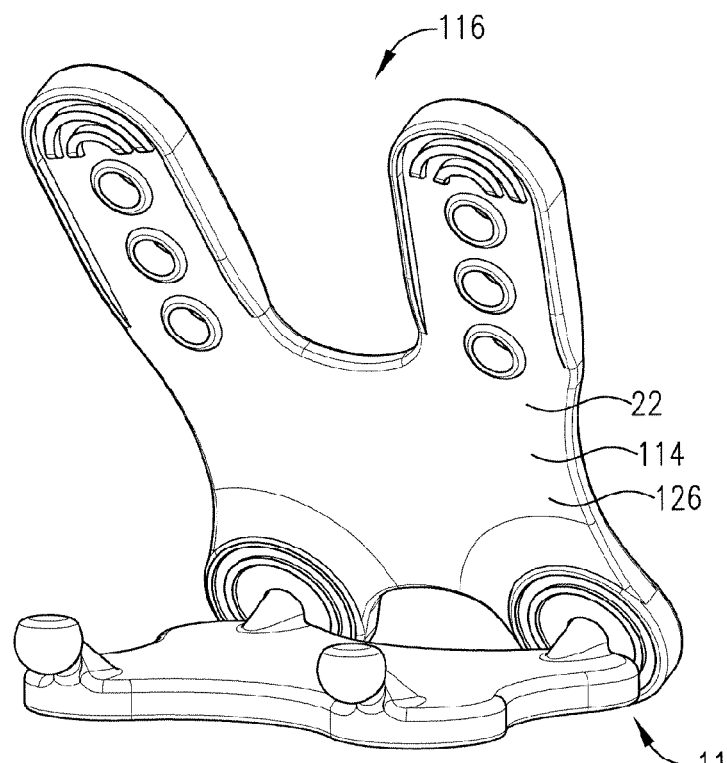
FIG. 7 is a perspective view of the intravenous catheter anchoring assembly, showing the platform and particularly the lower surface of the retaining strap.

Referring to FIGS. 6 and 7, the retaining strap 22 includes a body 114. The body 114 includes spaced apart opposite attachment ends 116, each formed by a pair of outwardly extending pull-tabs 118,120, and a centrally located stretch portion 122 between the ends 116. The body 114 presents upper and lower surfaces 124,126. The pull-tabs 118 provide a grasping surface for the retaining strap 22 and each provides an attachment location preferably in the form of a through-hole 128 for receiving a respective one of the connectors 92 as will be discussed. In the preferred embodiment, the pull-tabs 120 are adjustable and have an elongated shape to include three attachment locations, each in the form of through-hole 128. The body 114 includes reinforced edges 130 (preferably in the form of a raised rib extending about the perimeter) that surround respective holes 128 to enhance structural integrity and prevent tearing of the pull-tabs 118,120. The pull-tabs 118,120 enable grasping of the retaining strap 22 and further include grasping ribs 132 for that purpose. While the illustrated holes 128 are formed in pull-tabs 118,120, the principles of the present invention are also applicable where the holes 128 are formed in another portion of the body 114. Furthermore, with regard to certain aspects of the present invention, both or neither pair of tabs 118,120 can be provided with multiple attachment locations (or even only one tab could be provided with multiple attachment locations). In addition, the retaining strap 22 includes recessed scallops 134 between each of the pull-tabs 118,120.

Figure 5:
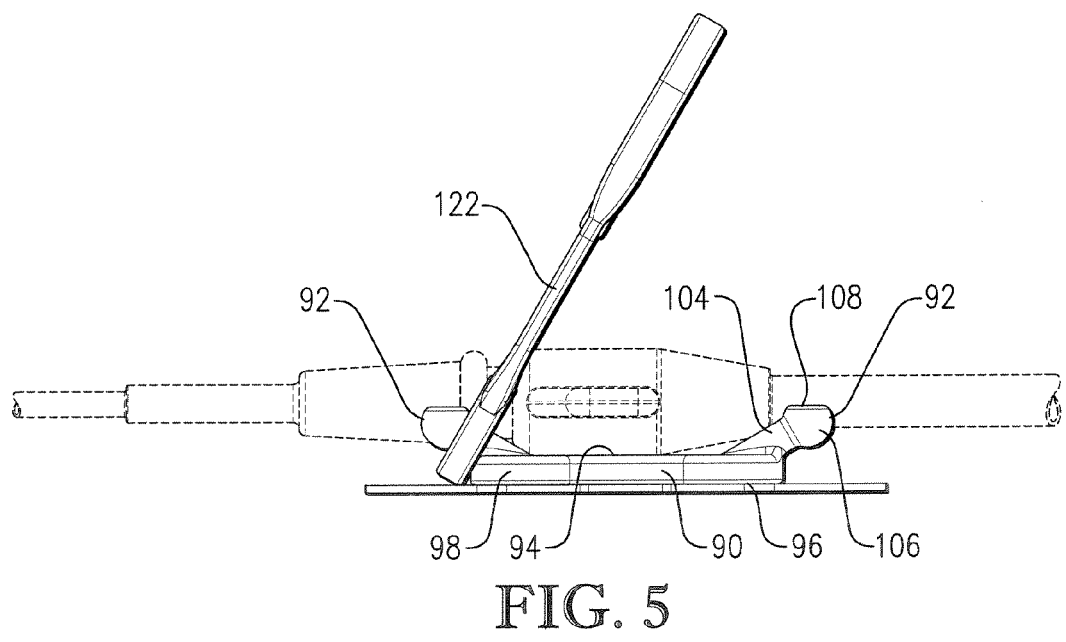
FIG. 5 is a side elevational view of the intravenous infusion site assembly shown in FIG. 3.

As perhaps best shown in FIGS. 5 and 6, the pull-tabs 118,120 and the stretch portion 122 give the retaining strap 22 a variable thickness. In particular, the pull-tabs 118,120 are about twice the thickness of the stretch portion 122 with the thickness tapering therebetween. Thus, the strain varies along the length of the body 114 so that the stretch portion 122 undergoes more elastic strain than the tabs 118,120 when a tensile load is applied to the retaining strap 22. Because strain is proportional to deformation, the stretch portion 122 will generally elastically elongate more than the tabs 118,120. While the body 114 is preferably formed of a substantially homogeneous material, it is also consistent with the principles of the present invention that the body 114 could include alternative materials to give the tabs 118,120 a generally greater modulus of elasticity than the remainder of the body. Such an alternative construction could involve forming the tabs with a relatively hard plastic material and the stretch portion 122 with an elastomer. In that situation, the stretch portion 122 would again undergo more elastic strain than the tabs 118,120 when a tensile load is applied. As will be apparent, the greatest degree of elastic stretching or elongation of the strap 22 occurs within the central portion 122 during use which facilitates the desired gripping of the catheter 12 or 16.

As discussed, the retaining strap 22 includes a substantially homogeneous material. More preferably, the retaining strap 22 is molded out of a substantially clear elastomeric silicon material. Also, the retaining strap 22 is preferably molded in an injection molding process. However, it could also be formed by other molding processes, such as thermoforming, known to those of ordinary skill in the art.

The elastomeric silicon material preferably includes a relatively high coefficient of friction and exhibits some "stickiness" on at least its catheter-engaging surfaces. Again, the use of elastomeric materials is preferred for enabling the intravenous catheter anchoring assembly 10 to frictionally engage the catheter 16. However, it is also preferred to coat portions of the elastomer surface of the retaining strap 22 with Parylene so that it is soft and has a relatively low coefficient of friction. For example, the outer, non-catheter-engaging surfaces of the retaining strap 22 are preferably coated so as to be soft and comfortable to the touch. Again, the Parylene coating is not preferred for the catheter-gripping surfaces of the illustrated retaining strap 22.

Figure 4:
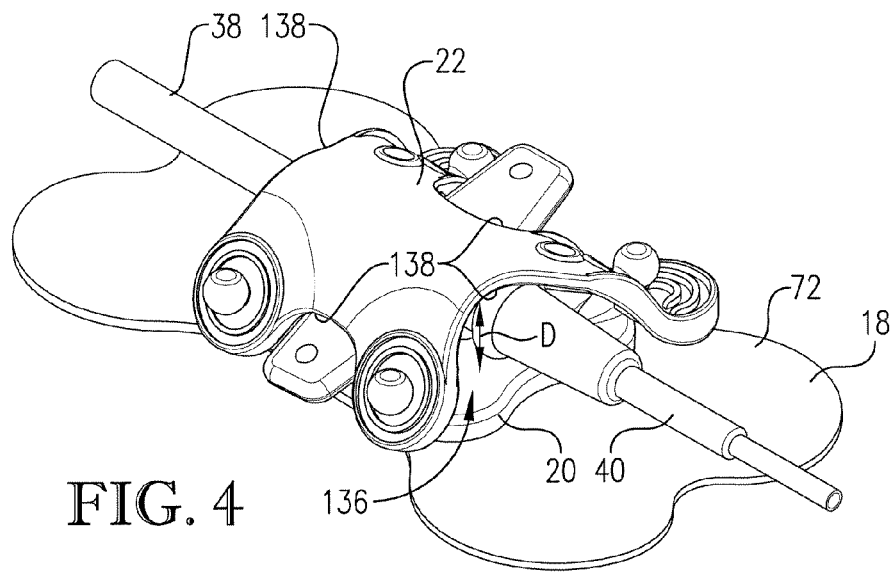
FIG. 4 is a perspective view of the intravenous infusion site assembly of FIGS. 1 and 2, particularly showing the securement of the catheter including the catheter suture hub in a lengthwise direction relative to the catheter anchoring assembly.

Turning to FIGS. 4, 5, and 7, the retaining strap 22 is initially attached to the platform 20 by preferably receiving two connectors 92 on one of the platform's sides 110 within respective pull-tabs 118. The rounded end 106 of post 104 is larger in diameter than the hole 128. Therefore, the elastic pull-tab 118 stretches outwardly so as to pass over end 106 and then be received on the post 104. The undersized hole 128 and rounded end 106 further restrict the pull-tab 118 from becoming unintentionally removed from the attached position. However, the flat 108 permits easier attachment and removal of the retaining strap 22 when the retaining strap is in a substantially upright orientation.

While the illustrated platform 20 includes the post 104 and the corresponding hole 128 is in the retaining strap 22, the platform 20 and retaining strap 22 could be variously configured to achieve a similar connecting mechanism without departing from the scope of the present invention. For example, either the platform 20 or retaining strap 22 could include one or more engageable posts, hooks, barbs, balls or other male projections. The other corresponding platform 20 or retaining strap 22 could then include corresponding holes, slots, sockets, or other female ends to achieve a removable connection with the respective male projections. Alternatively, the platform 20 or retaining strap 22 could each include a combination of male and female connectors consistent with the scope of the present invention.

Moreover, it is within the ambit of the present invention that the platform 20 and retaining strap 22 could be permanently attached to each other. For example, one or both ends 116 of the retaining strap 22 could be molded with, overmolded to, adhered to, or otherwise non-removably (e.g., integrally) fixed to the platform 20. The term coupled as used herein shall be interpreted to mean permanently attached, as discussed, or removably attached.

In the illustrated embodiment, the retaining strap 22 is fully secured to the platform 20 by lowering the pull-tabs 120 (causing the body 114 to flex) so that the remaining two connectors 92 can be received within two of the holes 128. The upwardly and outwardly angled posts 104 restrict the retaining strap 22 from moving out of the attached position, as the strap 22 would have to be stretched to a greater extent to do so. Again, each of the pull-tabs 120 includes a plurality of holes 128 for selective attachment to the connectors 92. Generally, each of the pull-tabs 120 can be attached to its respective connector 92 at the same time along any one of the holes 128. Thus, the retaining strap 22 is variously adjustable. Additionally, because the connectors 92 are about evenly spaced as discussed above, the retaining strap 22 is attachable to the platform 20 in any of four discrete orientations relative to the platform 20.

The elastomeric retaining strap 22 preferably includes a lower modulus of elasticity than the platform 20, making the retaining strap 22 less rigid than the platform 20. Therefore, when the retaining strap 22 is attached between connectors 92 under tension, the retaining strap 22 elongates while the platform 20 deflects negligibly. In this manner, the platform substantially retains its shape when the body is elastically stretched to receive the catheter 16.

Figure 3:
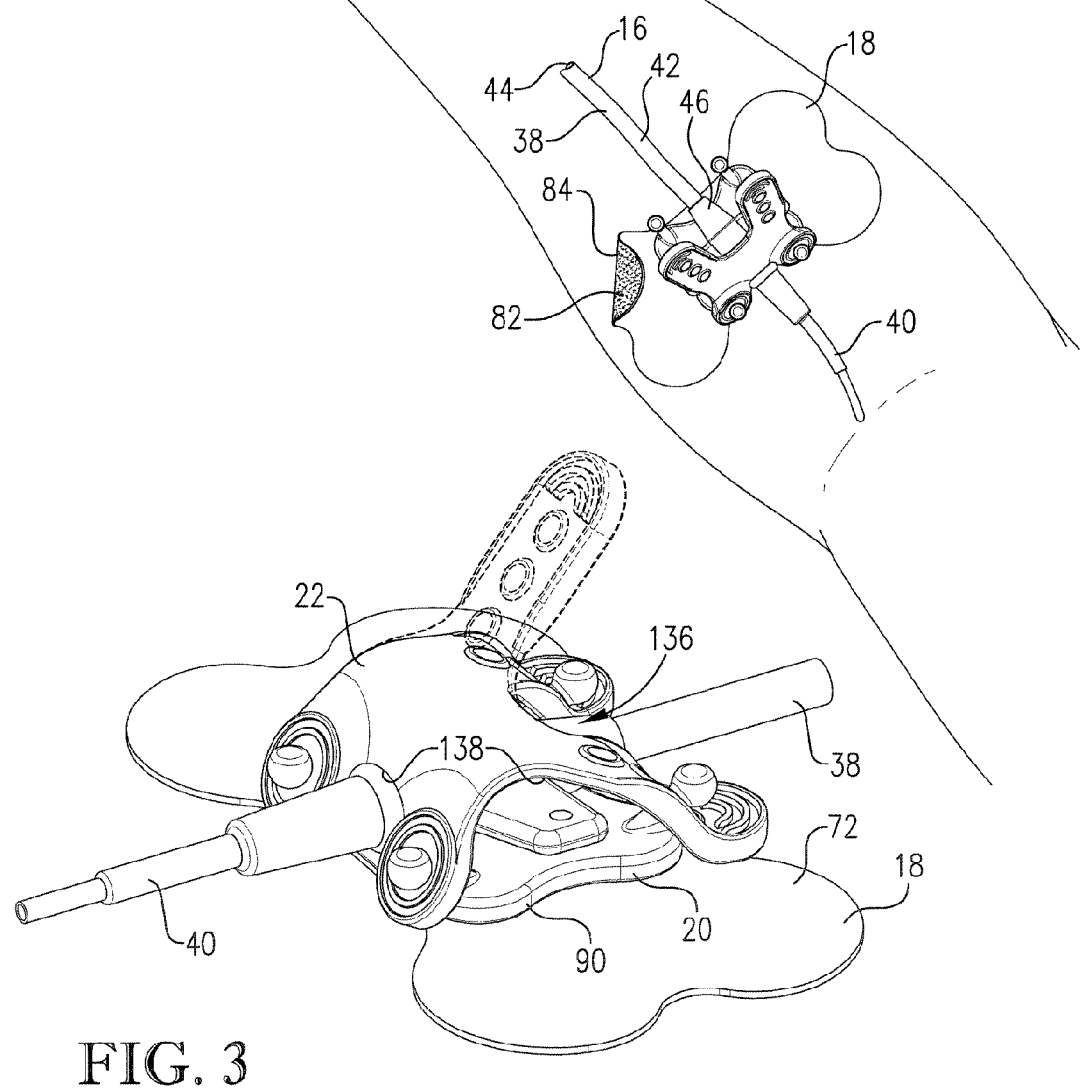
FIG. 3 is a perspective view of the intravenous infusion site assembly shown in FIGS. 1 and 2, particularly showing the securement of a catheter including a catheter suture hub in a transverse direction relative to the catheter anchoring assembly.

Turning to FIGS. 3-4, the attached retaining strap 22 and platform 20 form internal passageways 136 for receiving the catheter 16 so that the proximal and distal sections 38,40 project outwardly from the catheter anchoring assembly 10. The passageways 136 are defined by internal surfaces that receive and hold the catheter 16. Specifically, the upper surface 94 of platform 20, the connectors 92, and the lower surface 126 of retaining strap 22 provide these internal surfaces. Furthermore, the edges of these surfaces collectively form four discrete catheter-receiving openings 138. Each of the passageways 136 is defined by a respective pair of openings 138 and the internal surfaces. However, it is also consistent with the principles of the present invention for the passageways 136 to be defined by more than two openings 138. For example, a multi-lumen catheter may extend through three or more openings. In this manner, the passageways 136, although occupying the same volume, each provide a discrete path into and out of the catheter anchoring assembly 10. While the preferred embodiment includes four openings 138 and associated passageways 136, the principles of the present invention are equally applicable to including a greater or lesser number of openings 138 which are preferably and cooperatively defined by the platform 20 and strap 22.

The passageways 136 are also adjustably sized and shaped due to the adjustable and elastic features of the retaining strap 22. More specifically, the passageways 136 have an adjustable cross-sectional dimension D (see FIG. 4). The illustrated dimension D is the maximum internal height between the platform 20 and the retaining strap 22. However, the passageways 136 include other adjustable cross-sectional dimensions (not shown) between the retaining strap 22 and the platform 20. The dimension D varies depending on which of the three holes 128 in pull-tabs 120 receive the respective connector 92. The dimension D also varies depending on the size and shape of the received catheter 16.

The catheter anchoring assembly 10 secures the catheters 12,16 as shown in FIGS. 1-5. In FIG. 1, the catheter 12 is secured by arranging the Y-site suture hub 26 between the platform 20 and the retaining strap 22. In FIGS. 2 and 3, the catheter 16 is aligned substantially orthogonally to the longitudinal axis of the membrane 18 and platform 20. As discussed, the retaining strap 22 is partially attached to the platform 20 with connectors 92 being received in holes 128 of the tabs 118. Most preferably, an edge of the retaining strap 22 is received within the annular groove 56 to further restrict axial movement of the catheter 16.

The pull-tabs 120 are then secured to the remaining connectors 92 by stretching the retaining strap 22 over the suture hub 46. The platform 20 and strap 22 are preferably configured and dimensioned so that the strap 22 is elastically stretched when the catheter is secured between the platform 20 and strap 22, whereby the catheter 16 is gripped and axially retained. The suture hub 46 is arranged between the platform 20 and retaining strap 22 with the tubing 42 extending through oppositely spaced openings 138 and across the primary attachment sides 110. Furthermore, projections 50 are received respectively in the remaining oppositely spaced openings 138. Again, the fully attached retaining strap 22 is preferably elastically elongated and under tension to force the catheter 16 against the platform 20. This elongation further promotes the gripping ability of the retaining strap 22 by increasing the frictional engagement between the retaining strap 22 and catheter 16. Elongation and stretching around the catheter 16 also promotes gripping in that the retaining strap 22 conforms more closely to the contours of the catheter 16. The illustrated retaining strap 22 and platform 20 grip the catheter 16 to restrict movement along the catheter's axial direction but also along a transverse or vertical direction. Moreover, the catheter 12 is substantially restricted from rotating in any direction. However, it is consistent with certain aspects of the present invention that the retaining strap 22 could be attached to retain the catheter 16 without being elongated or otherwise elastically stretched.

Referring to FIG. 4, the illustrated catheter 16 is aligned with the longitudinal axis of the membrane 18 and platform 20 in an alternative and orthogonal orientation relative to the orientation of the catheter 16 shown in FIG. 3. Again, the retaining strap 22 is stretched around the suture hub 46 and grips the catheter 16. The tubing 42 extends through a pair of oppositely spaced openings 138, but across the secondary attachment sides 112. Projections 50 are received in the remaining oppositely spaced openings 138. Therefore, the catheter 16 is permitted to be secured in any of four discrete orientations with respect to the platform 20. The selectable orientations permit the membrane 18 and platform 20 to be variously arranged on patient P for optimizing the patient's comfort or the adhering strength between the membrane 18 and the patient's skin with minimal effect on the desired catheter orientation.

In operation, the catheter 16 is inserted into the patient P (see FIG. 2) and then arranged relative to the patient's arm A. Although the illustrated catheter 16 is shown in association with the patient's arm, other peripheral locations (e.g., the leg, foot, etc.) are entirely within the ambit of the present invention. The proximal section 26 extends toward and connects to an intravenous fluid administration set (not shown). The catheter anchoring assembly 10 is arranged under the catheter 16 in the desired orientation. Once positioned, the catheter anchoring assembly 10 is adhered to the patient's skin adjacent to the puncture location 30. Obviously, one important advantage of the assembly 10 is the ability to securely fix the catheter 16 to the patient without requiring the use of sutures, which significantly increase patient discomfort and the risk of infection. The catheter 16 extends across the platform 20 with the projections 50 spaced between the connectors 92. The retaining strap 22 is initially attached to the platform 20 so that the retaining strap 22 secures the catheter 16 between two of the connectors 92. The retaining strap 22 is then elastically stretched across the platform 20 and secured to the remaining connectors 92. Thus, the catheter 16 is secured so that the tubing 42 is secured in two oppositely spaced openings 138 and the projections 50 are secured in the other two oppositely spaced openings 138.

The elongated pull-tabs 120 can be re-attached to the connectors 92 to change the amount of elastic elongation in the retaining strap. In this manner, the catheter 16 can be more tightly or loosely secured. Such reattachment not only permits the catheter-receiving passageway to be adjustably sizeable, but with the elastic nature and stretching of the strap 22, the gripping force applied against the catheter 16 can be varied. The pull-tabs 118,120 can be released to permit removal of the catheter 16 from the catheter anchoring assembly 10.

Turning to FIGS. 8-26, alternative embodiments of the present invention are depicted. For the sake of brevity, the remaining description will focus primarily on the differences of these alternative embodiments from the preferred embodiment.

Figure 8:
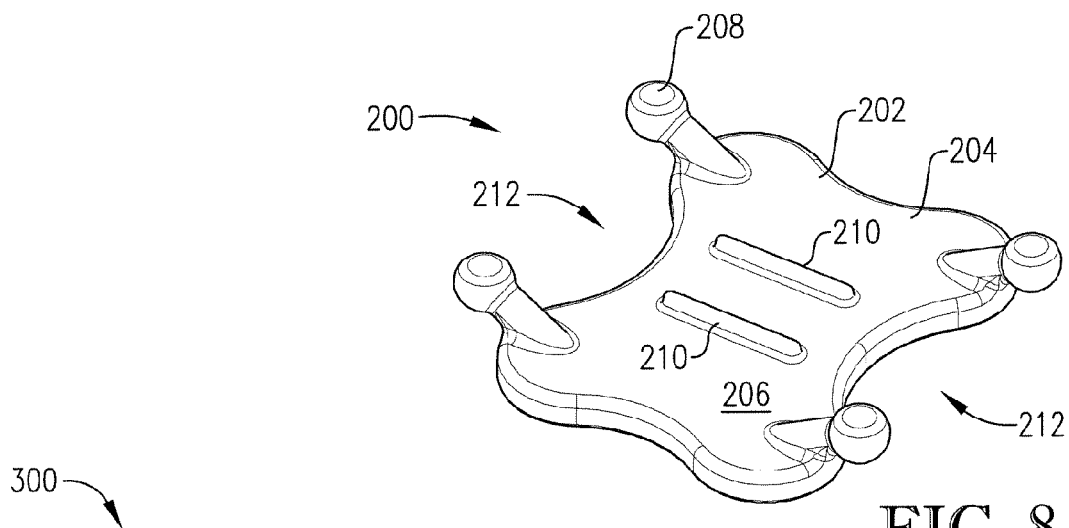
FIG. 8 is a perspective view of a second embodiment of the intravenous catheter anchoring assembly showing a first alternative platform.
Figure 9:
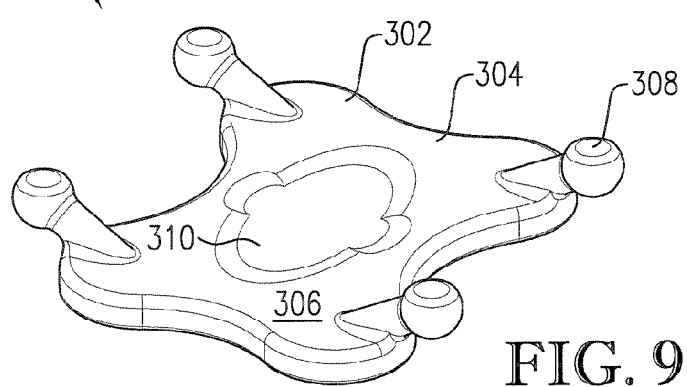
FIG. 9 is a perspective view of a third embodiment of the intravenous catheter anchoring assembly showing a second alternative platform.

FIGS. 8-9 illustrate two alternative embodiments of the present invention. These alternative embodiments are directed to alternative platforms having an alternatively shaped base as will be discussed.

In FIG. 8, a second embodiment of the present invention is an intravenous catheter anchoring assembly 200 including an alternative platform 202. The platform 202 includes a base 204 presenting an upper surface 206 and connectors 208. The base 204 further includes rib-like protrusions 210 forming part of the upper surface 206. The protrusions 210 are parallel to each other and extend between primary attachment sides 212 of the platform 202 for securing the catheter (not shown) therebetween. The protrusions 210 are preferably molded with the rest of the base 204, but could alternatively be machined or separately formed and then attached without departing from the principles of the present invention.

In FIG. 9, a third embodiment of the present invention is an intravenous catheter anchoring assembly 300 including an alternative platform 302. The platform 302 includes a base 304 presenting an upper surface 306 and connectors 308. The base 304 further includes a concave depression 310 defining a curvilinear portion of the upper surface 306. The shape of the depression 310 is preferably configured to receive the catheter hub (not shown). While the illustrated depression 310 is shaped to receive a variety of catheter hubs, the depression 310 could be alternatively shaped to receive a particular catheter hub so that the depression 310 is form-fitting. The depression 310 is preferably molded with the rest of the base 304 but could also be machined or separately formed and then attached to the upper surface 306.

FIGS. 10-14 illustrate several alternative embodiments of the present invention. These alternative embodiments are directed to anchoring assemblies incorporating alternative retaining straps.

Figure 10:
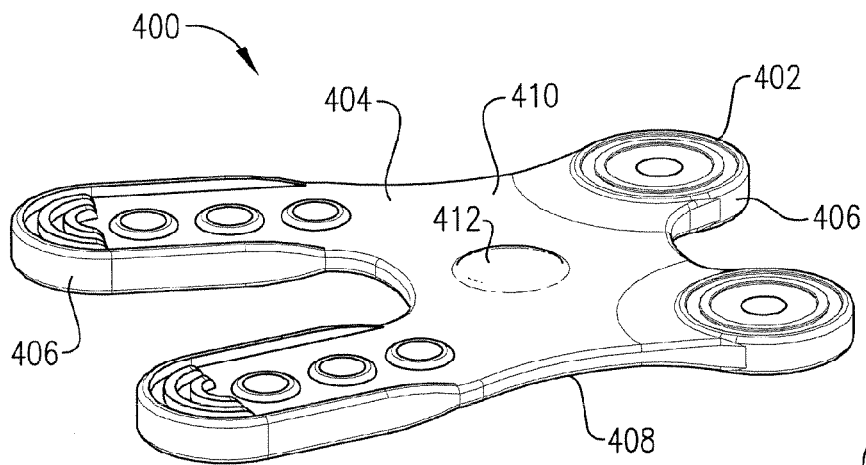
FIG. 10 is a perspective view of a fourth embodiment of the intravenous catheter anchoring assembly showing a first alternative retaining strap.

In FIG. 10, a fourth embodiment of the present invention is an intravenous catheter anchoring assembly 400 including an alternative retaining strap 402. The retaining strap 402 comprises a body 404 including pull-tabs 406 and presenting upper and lower surfaces 408,410. The body 404 further includes a spherical protrusion 412 forming part of the lower surface 410. The protrusion 412 is shaped to press against the catheter hub (not shown) when the retaining strap 402 is coupled to the platform (not shown). The protrusion 412 is preferably compressible to the extent that it is compressed during use of the assembly 400, whereby gripping of the catheter is further enhanced.

Figure 11:
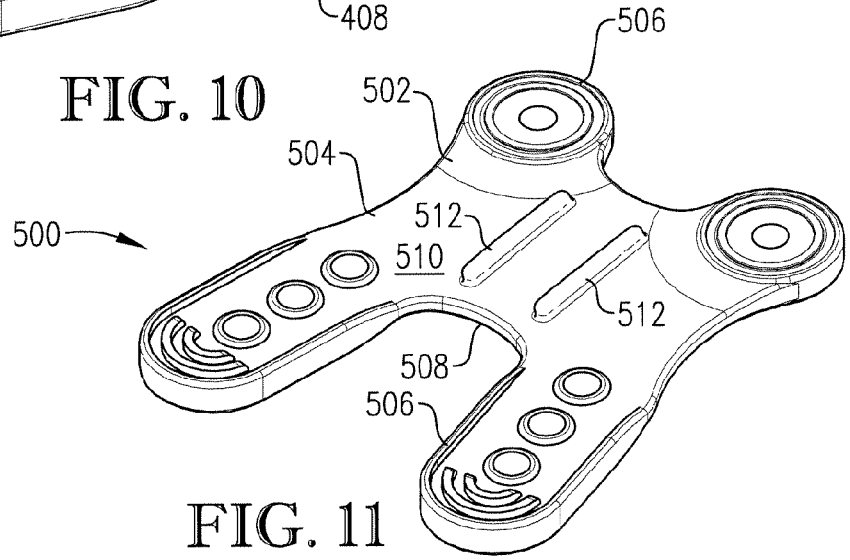
FIG. 11 is a perspective view of a fifth embodiment of the intravenous catheter anchoring assembly showing a second alternative retaining strap.

In FIG. 11, a fifth embodiment of the present invention is an intravenous catheter anchoring assembly 500 including an alternative retaining strap 502. The retaining strap 502 comprises a body 504 including pull-tabs 506 and presenting upper and lower surfaces 508,510. The body 504 further includes rib-shaped protrusions 512 that are parallel to each other. The protrusions 512 form part of the lower surface 510 for receiving the catheter (not shown). Moreover, the protrusions 512 preferably function similar to the protrusion 412 shown in FIG. 10.

Figure 12:
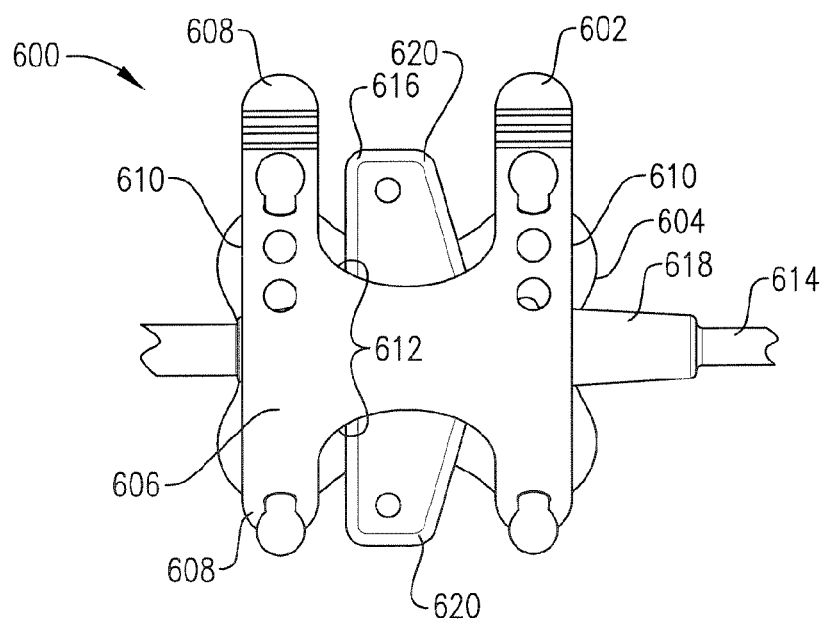
FIG. 12 is a top view of a sixth embodiment of the intravenous catheter anchoring assembly, showing a third alternative retaining strap that is H-shaped.

In FIG. 12, a sixth embodiment of the present invention is an intravenous catheter anchoring assembly 600 including an alternative retaining strap 602 and a platform 604. The retaining strap 602 comprises a body 606 including pull-tabs 608. The body 606 has a generally H-shaped configuration with all of the pull-tabs 608 being generally elongated. The retaining strap 602 cooperates with the platform 604 to form a first pair of substantially identical catheter-receiving openings 610 and a generally transverse second pair of substantially identical catheter-receiving openings 612. A catheter 614 includes a catheter hub 616 with a body 618 and projections 620. The illustrated openings 610,612 receive ends of the body 618 and projections 620 respectively. However, the openings 610,612 permit the catheter 614 to be secured in one of four discrete orientations.

Figure 13:
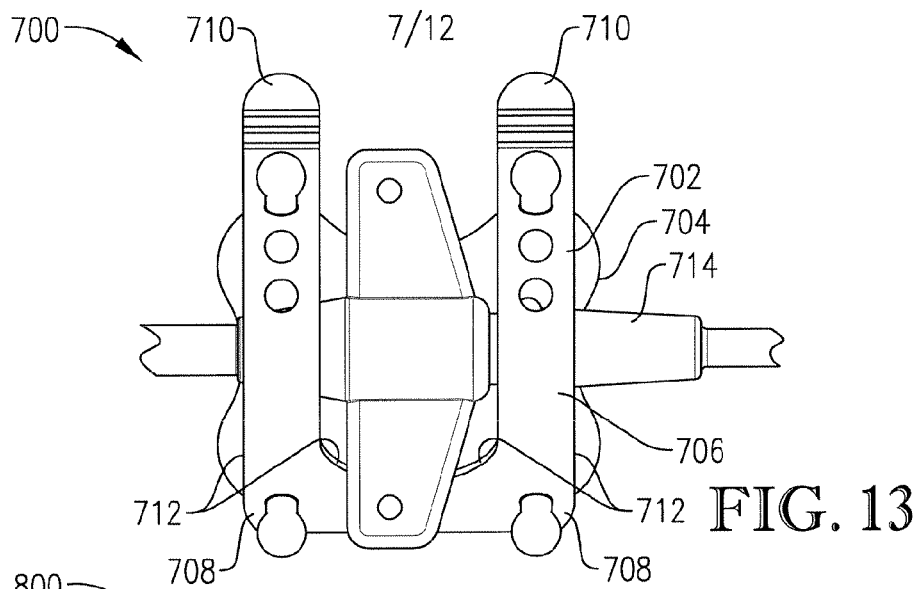
FIG. 13 is a top view of a seventh embodiment of the intravenous catheter anchoring assembly, showing a fourth alternative retaining strap that is U-shaped.

In FIG. 13, a seventh embodiment of the present invention comprises an intravenous catheter anchoring assembly 700 including an alternative retaining strap 702 and a platform 704. The retaining strap 702 comprises a body 706 including pull-tabs 708,710. The body 706 has a generally U-shaped configuration. The retaining strap 702 cooperates with the platform 704 to provide openings 712 and corresponding passageways through which a catheter 714 is received.

Figure 14A:
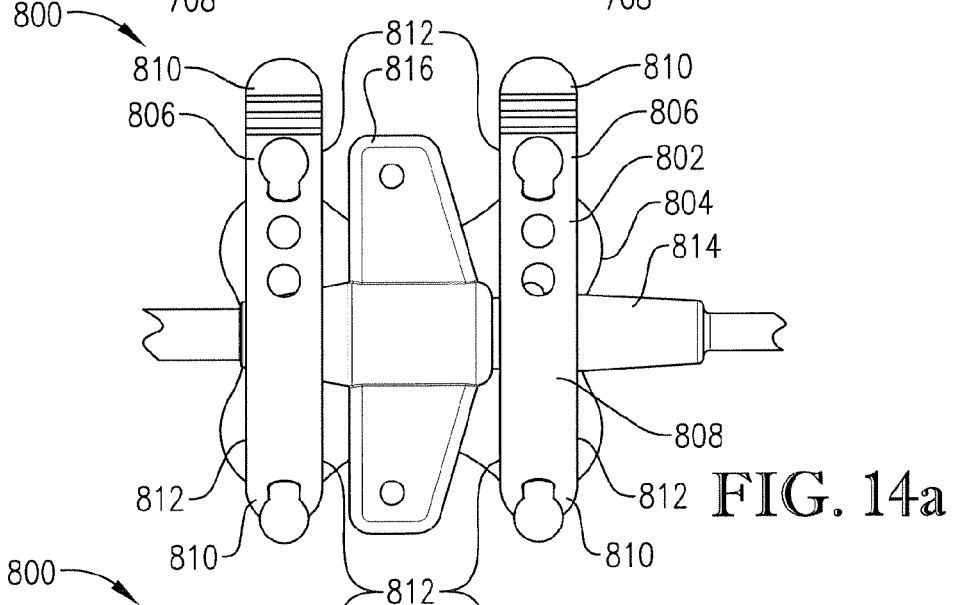
FIG. 14a is a top view of an eighth embodiment of the intravenous catheter anchoring assembly, showing a fifth alternative retaining strap that includes non-unitary strap portions secured in a parallel relationship.
Figure 14B:
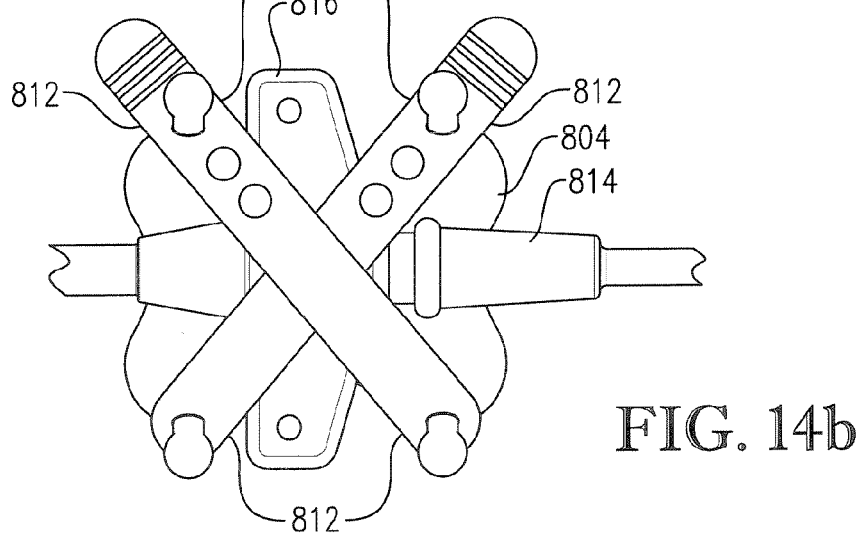
FIG. 14b is a top view of the intravenous catheter anchoring assembly shown in FIG. 14, but illustrating the non-unitary strap portions secured in an overlying relationship.

In FIGS. 14a and 14b, an eighth embodiment of the present invention is an intravenous catheter anchoring assembly 800 including an alternative retaining strap 802 and platform 804. The retaining strap 802 includes non-unitary strap portions 806, where each of the elongated portions 806 comprises a body 808 including pull-tabs 810. As depicted in FIG. 14a, the portions 806 are attached to the platform 804 in a substantially parallel relationship so that four catheter-receiving openings 812 are formed between the platform 804 and retaining strap 802, each opening extending along a corresponding side of one of the strap portions 806. The strap portions 806 essentially define two passageways, with the catheter 814 preferably being received in both passageways simultaneously. The catheter 814 includes wings 816 that are not received in the passageways. As depicted in FIG. 14b, the portions 806 are attached to the platform 804 in a crossing (X-shaped) relationship so that four catheter-receiving openings 812 are formed and define a plurality of passageways. The openings 812 are generally V-shaped in plan view. The catheter 814 and catheter wings 816 are received within the passageways.

FIGS. 15-20 illustrate several alternative embodiments of the present invention. These embodiments are directed to alternative platform and retaining strap combinations.

Figure 15:
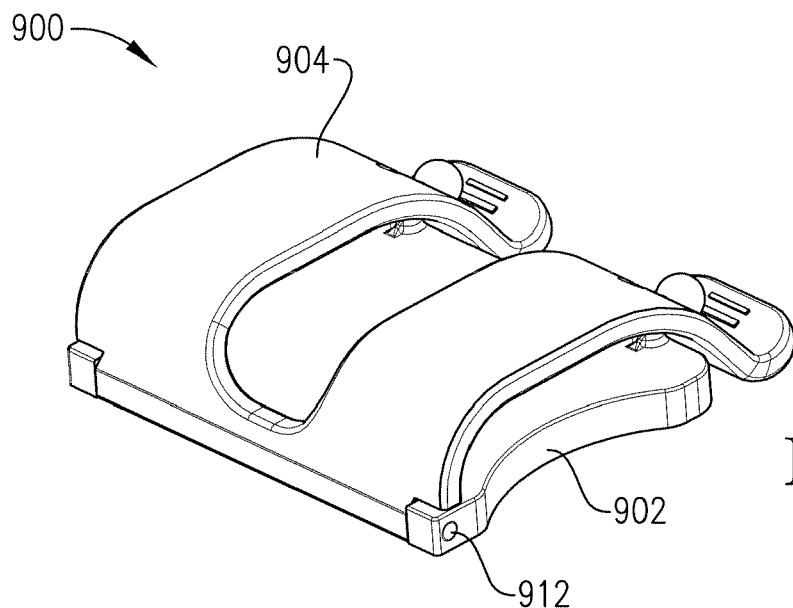
FIG. 15 is a perspective view of a ninth embodiment of the intravenous catheter anchoring assembly, showing a sixth alternative retaining strap and a third alternative platform that are hingedly connected.
Figure 16:
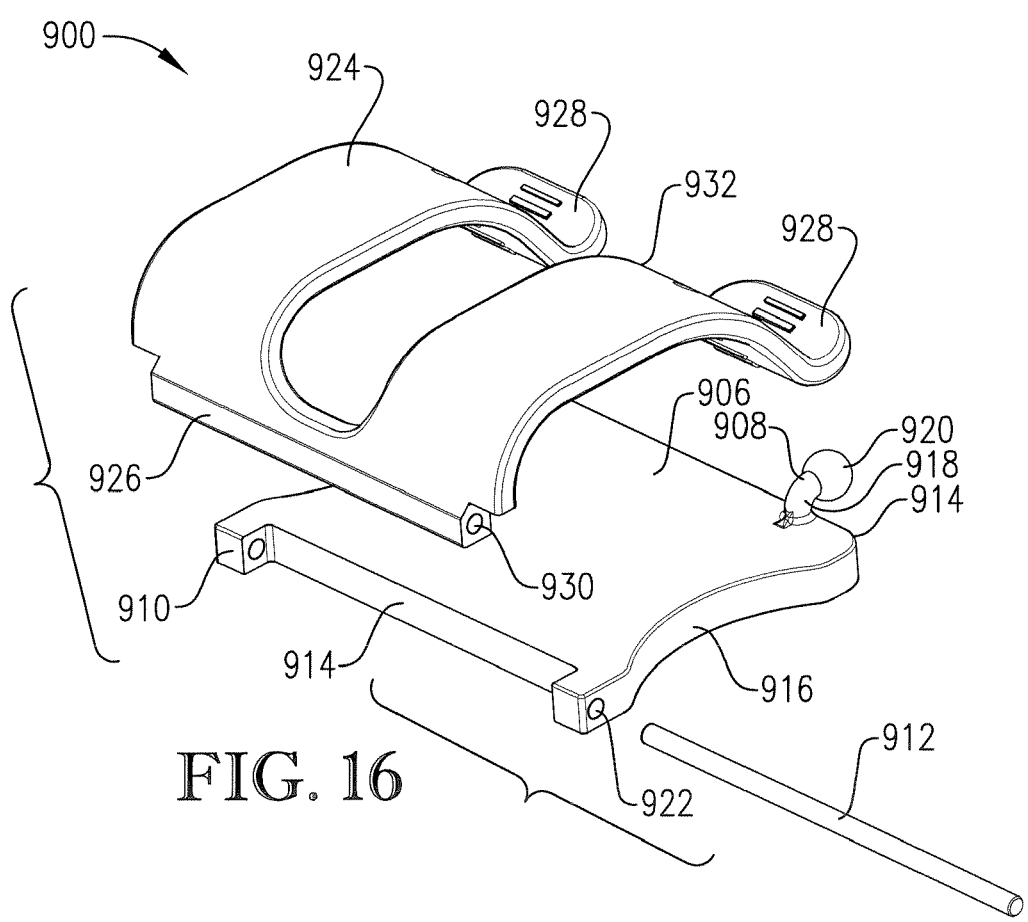
FIG. 16 is an exploded perspective view of the intravenous catheter anchoring assembly shown in FIG. 15.

Referring to FIGS. 15 and 16, a ninth embodiment of the present invention is an intravenous catheter anchoring assembly 900 including an alternative platform 902 and an alternative retaining strap 904. The platform 902 includes a base 906, connectors 908,910, and pin 912. The base 906 is flat and generally rectangular-shaped with straight edges 914 and scalloped edges 916. Along one of the straight edges 914, connectors 908 extend out and include a post 918 with a spherical end 920. The post 918 is curved and extends upwardly and outwardly from the base 906. Along the other straight edge 914, connectors 910 extend laterally out from the base 906 and include aligned holes 922. The holes 922 rotatably receive the pin 912.

The U-shaped retaining strap 904 includes a body 924 presenting an attachment end 926 and pull-tabs 928. The attachment end 926 includes a bore 930 that receives the pin 912. In this manner, the retaining strap 904 and platform 902 are partially attached to each other by a hinge. The pin 912 is preferably rotates relative to the retaining strap 904 when the strap 904 and platform 902 are assembled. However, it is also consistent with the principles of the present invention for the pin 912 to rotate relative to either or both the strap 904 and platform 902. The retaining strap 904 is further attached to the platform 902 by securing the connectors 908 within respective holes 932 of the pull-tabs 928. Although not shown, each of the tabs 928 can be provided with multiple holes 932 to afford the adjustability noted above.

Referring to FIGS. 17 and 18, a tenth embodiment of the present invention concerns an intravenous catheter anchoring assembly 1000 including an alternative platform 1002 and an alternative retaining strap 1004. The platform 1002 includes a base 1006 and connectors 1008,1010. Connectors 1008 include recessed hooks 1012 projecting laterally from the base 1006 and turning downward. Connectors 1010 project upwardly and outwardly from the base 1006 and include a post 1014 with an enlarged spherical head 1016. The U-shaped retaining strap 1004 comprises a body 1018 presenting an attachment end 1020 and pull-tabs 1022. The attachment end 1020 includes slotted holes 1024 that each receive a respective one of the hooks 1012. Each pull-tab 1022 includes a pair of rounded holes 1026 that are undersized relative to the spherical head 1016.

Turning to FIGS. 19 and 20, an eleventh embodiment of the present invention comprises an intravenous catheter anchoring assembly 1100 including an alternative platform 1102 and an alternative retaining strap 1104, which are similar to that shown in FIGS. 17 and 18. The platform 1102 includes a base 1106 and connectors 1108,1110. Connectors 1108 include recessed hooks 1112 projecting laterally from the base 1106. Connectors 1110 project upwardly and outwardly from the base 1106 and include a post 1114 having a rectangular cross-section. The rectangular-shaped retaining strap 1104 comprises a body 1116 including an attachment end 1118 and a single pull-tab 1120. The attachment end 1118 and pull-tab 1120 include slotted holes 1122 that each receive a respective one of the connectors 1110. The body 1116 is generally solid and rectangular in shape, such that discrete pull-tabs are not defined.

FIGS. 21-24 illustrate two alternative embodiments of the present invention. These embodiments principally perform the function of a tubing collector, but they also have features which restrict axial movement of the tubing, such that they might also serve as site securement devices.

Figure 21:
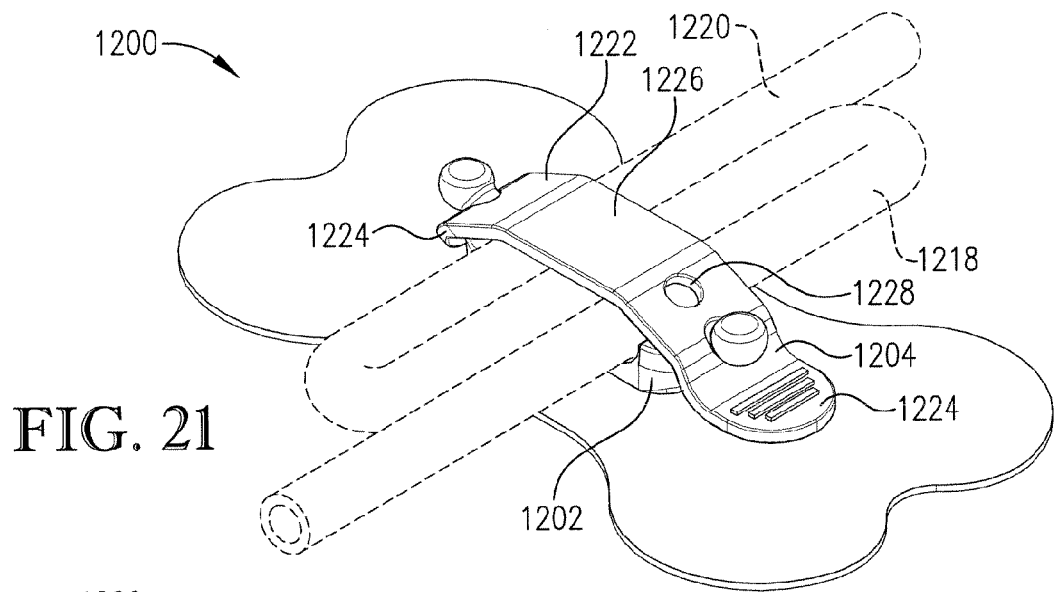
FIG. 21 is a perspective view of a twelfth embodiment of the intravenous catheter anchoring assembly, wherein the assembly comprises a tubing collector.
Figure 22:
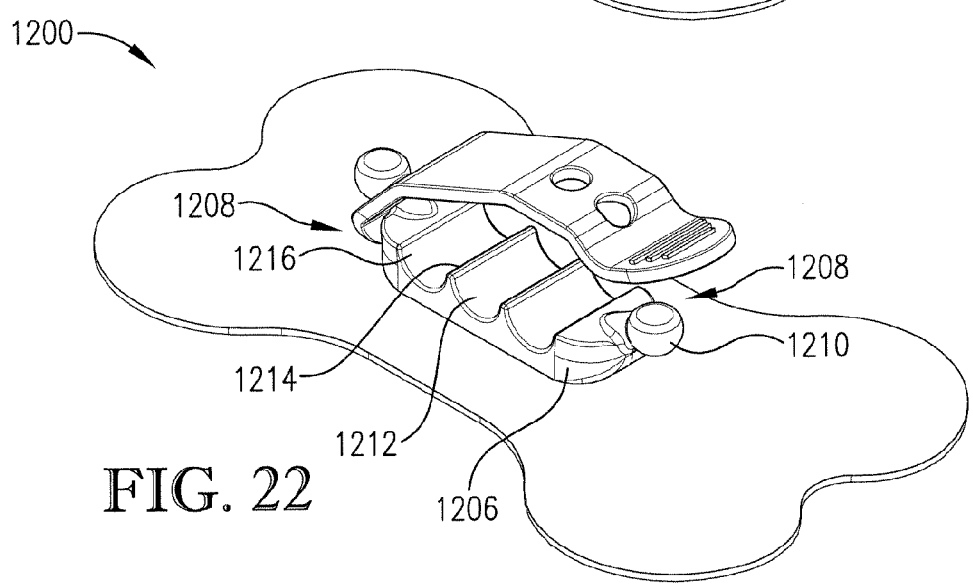
FIG. 22 is a perspective view of the intravenous catheter anchoring assembly shown in FIG. 21 with the retaining strap partially detached from the platform and the catheter tubing removed.

In FIGS. 21 and 22, a twelfth embodiment of the present invention concerns an intravenous catheter anchoring assembly 1200 including an alternative platform 1202 and an alternative retaining strap 1204. The platforms 202 includes an elongated base 1206 with ends 1208. The platform 1202 further includes connectors 1210 extending from the ends 1208. Between the ends 1208 are arcuate troughs 1212 that have a semi-circular cross-section. The troughs 1212 are substantially parallel and are separated by ridges 1214. The arcuate troughs 1212 run orthogonally to the longitudinal axis of the base 1206. The troughs 1212 and ridges 1214 form part of an upper surface 1216 that provides discrete locations for receiving tubing 1218 (see FIG. 21). The illustrated tubing 1218 is part of an intravenous administration set 1220. However, it is consistent with the principles of the present invention that the tubing 1218 could be part of an extension set or could be catheter tubing.

The retaining strap 1204 comprises a body 1222 with pull tabs 1224, a stretch portion 1226, and through-holes 1228. The tubing 1218 is preferably arranged in a serpentine pattern such that each trough 1212 receives a section of the tubing 1218. The strap 1204 is then stretched over the arranged tubing 1218 to hold the tubing 1218 within the troughs 1212 and thereby restrict movement out of the troughs 1212 and axial movement through the troughs 1212.

Figure 23:
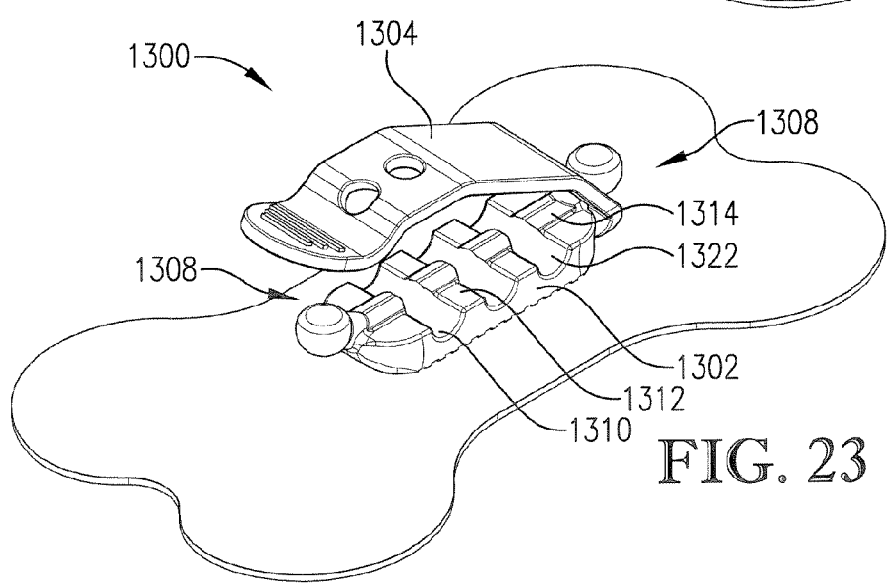
FIG. 23 is a perspective view of a thirteenth embodiment of the intravenous catheter anchoring assembly, similar to that shown in FIGS. 21 and 22, but with the platform being alternatively configured.
Figure 24:
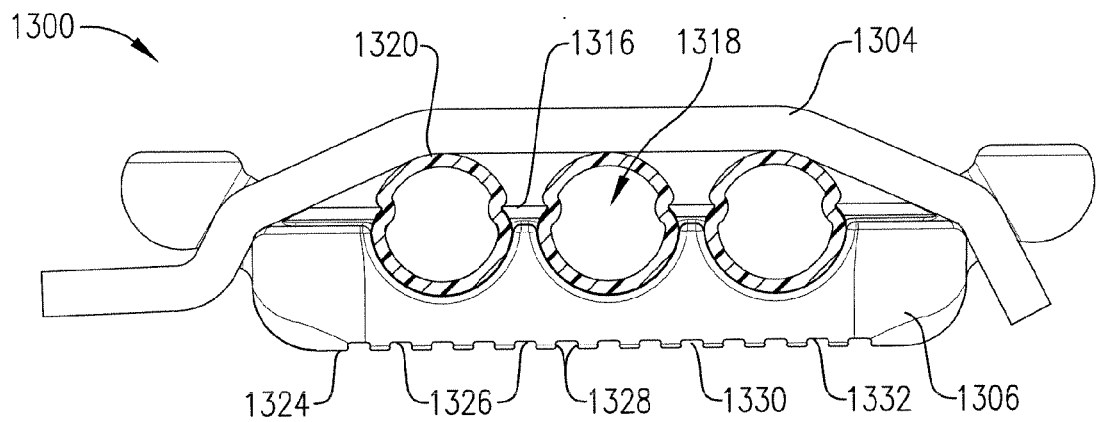
FIG. 24 is a side view of the intravenous catheter anchoring assembly shown in FIG. 23, illustrating the retaining strap attached to the platform to secure tubing therein and the grooved lower surface of the platform.

In FIGS. 23 and 24, a thirteenth embodiment of the present invention comprises an intravenous catheter anchoring assembly 1300 including an alternative platform 1302 and a retaining strap 1304, which are similar to that shown in FIGS. 21 and 22. The platform 1302 includes a base 1306 with ends 1308. Between the ends 1308 are arcuate troughs 1310 separated by ridges 1312. The troughs 1310 each have a substantially semi-circular cross-section (preferably defined by an arc of about 180) and include a maximum width. However, the principles of the present invention are equally applicable to a trough cross-section that is smaller or larger than 180. A longitudinal ridge 1314 runs between the ends 1308 and over the ridges 1312 to form catches 1316 on each side of each trough 1310 that project radially inward relative to the arc.

The illustrated catches 1316 cooperate with the troughs 1310 to define undercut sides and restricted openings 1318 that are smaller in width than the trough's maximum width and undersized relative to the diameter of tubing 1320 (see FIG. 24). In this manner, the troughs 1310, ridges 1312, and catches 1316 form an upper surface 1322 of the platform 1302 for receiving catheter tubing 1320 and releasably retaining the tubing 1320 within the troughs 1310. In particular, the catches 1316 permit various sizes of tubing 1320 to be partially secured in the catheter anchoring assembly 1300 prior to completed attachment of the retaining strap 1304. This enables the patient to single-handedly secure the tubing 1320 by attaching the retaining strap 1304 without having to simultaneously hold the tubing 1320 in place. In essence the tubing 1320 is "snapped" into the troughs 1310 with the catches 1316 slightly deforming the tubing 1320 and thereby gripping it in place. Such gripping further restricts axial movement of the tubing. The principles of the present invention are also applicable to other trough shapes that provide restricted openings, such as a trough cross-section with a circular arc of greater than 180 or a non-circular shape with an opening smaller than its maximum width.

The platform 1302 further includes a lower surface 1324. The base 1306 includes a plurality of parallel grooves 1326 extending between sides of the platform 1302. The grooves 1326 have undercut sides 1328 (similar to a dove-tail cross-section) to form a narrow opening 1330 and a slightly wider base 1332. The grooves 1326 increase the base's surface area to promote adhesion to the flexible membrane (not shown). The shape of the grooves 1326 also permit adhesive to be received therein such that the adhesive layer is mechanically and adhesively attached to the platform 1302.

Figure 26:
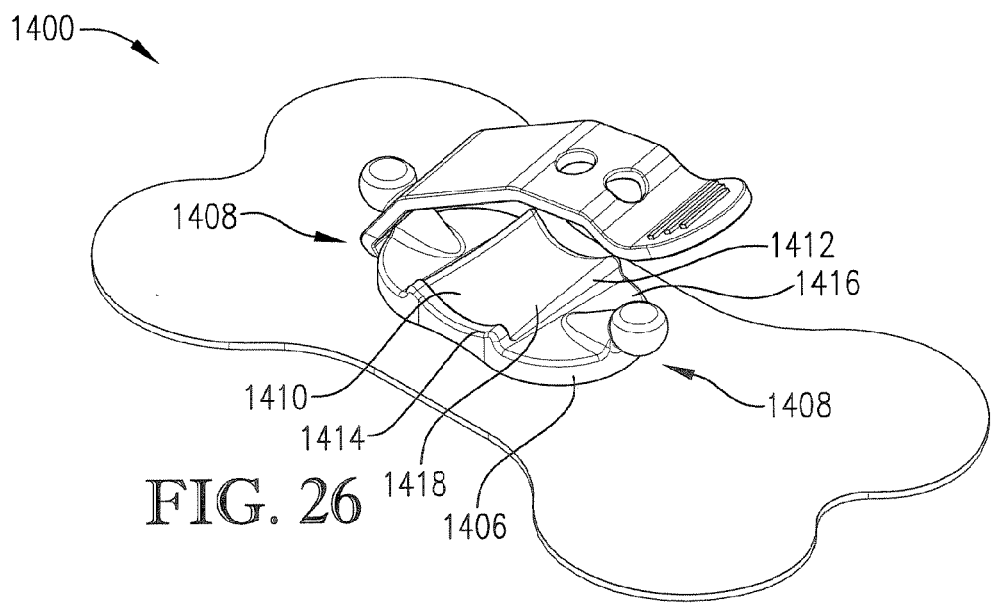
FIG. 26 is a perspective view of the intravenous catheter anchoring assembly shown in FIG. 25, with the retaining strap partially detached and the catheter removed.

In FIGS. 25 and 26, a fourteenth embodiment of the present invention comprises an intravenous catheter site securement device 1400 specifically designed for securing the alternative catheter 44. The catheter anchoring assembly 1400 includes an alterative platform 1402 and a retaining strap 1404. The platform 1402 includes a base 1406 with ends 1408. The base includes, between the ends 1408, an arcuate trough 1410, spaced apart ridges 1412, and a stop 1414 located at one end of the trough 1410. The base 1406 includes an upper surface 1416. The trough 1410 forms an inclined section 1418 of the upper surface 1416.

The platform 1402 and retaining strap 1404 receive the catheter hub 48 and secure it within the trough 1410 so that it is inclined toward the stop 1416. In this manner, the strap which is preferably elastically stretched urges the hub 48 against the inclined trough 1410 downwardly toward and against the stop 1416. Thus, the stop 1416 resists axial movement of the catheter 44 beyond the stop 1416, and the inclined trough resists axial movement of the catheter 44 away from the stop 1416. The restricted axial movement also restricts pistoning of the catheter 44.

Figure 27:
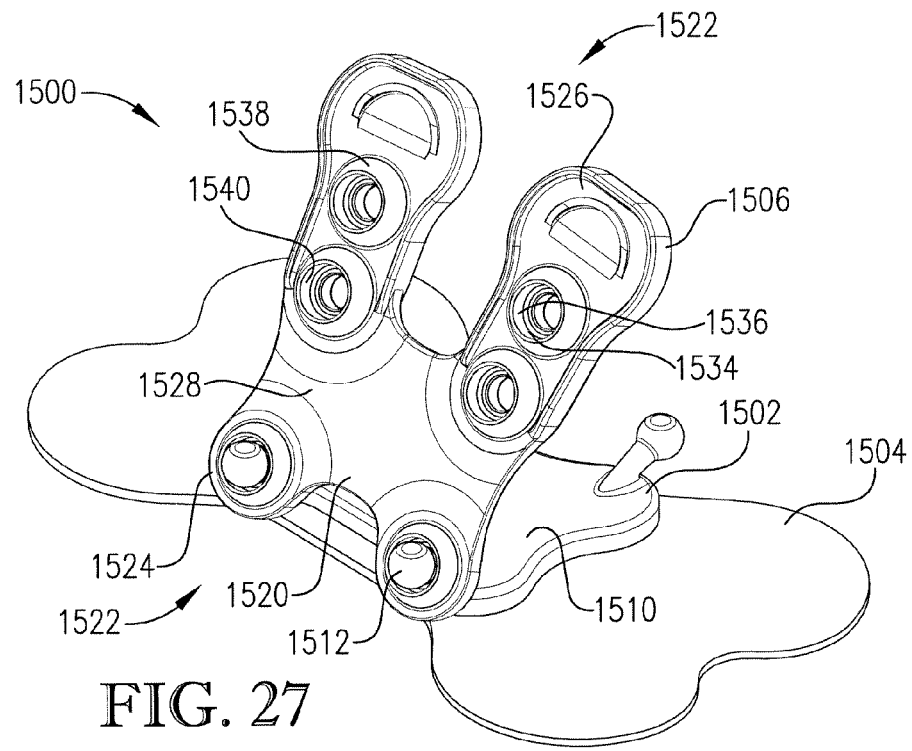
FIG. 27 is a perspective view of a fifteenth embodiment of the intravenous catheter anchoring assembly, which comprises a site securement device for securing a catheter.
Figure 28:
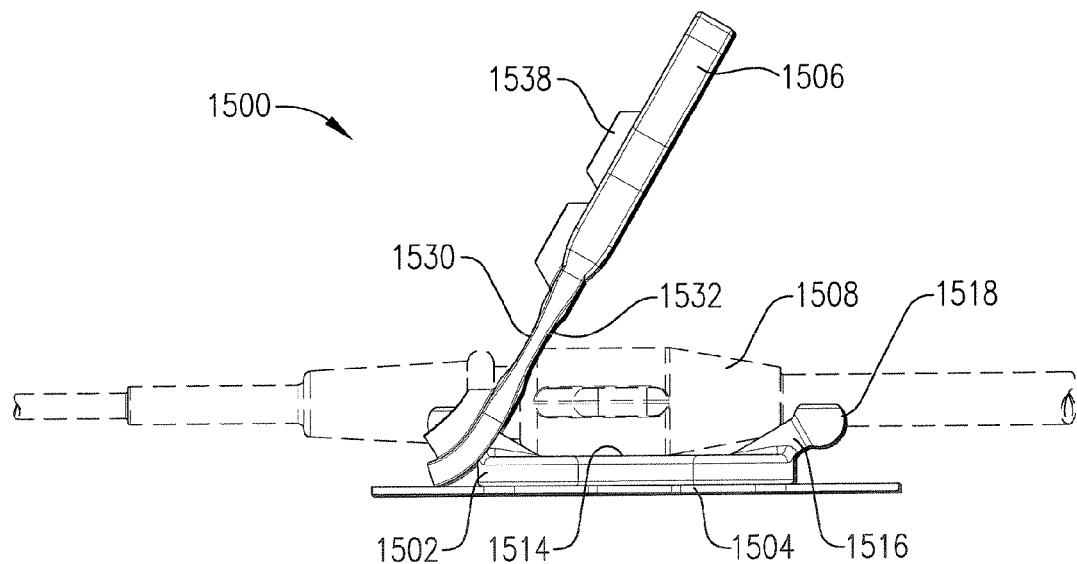
FIG. 28 is a side view of the intravenous catheter anchoring assembly shown in FIG. 27, showing the retaining strap partially attached to the platform with the catheter positioned therebetween.

FIGS. 27-28 illustrate a fifteenth embodiment of the present invention. The alternative embodiment functions primarily as an intravenous site securement device. However, the principles of this embodiment are equally applicable to other intravenous anchoring devices such as tubing collectors.

In FIG. 27, an intravenous catheter anchoring assembly 1500 includes a platform 1502, a patient-contacting membrane 1504, and an alternative retaining strap 1506 for securing the catheter 1508 (see FIG. 28). The platform 1502 includes a base 1510 and connectors 1512 and further presents an upper surface 1514. The connectors 1512 include a post 1516 with a head end 1518.

The retaining strap 1506 includes a body 1520. The body 1520 includes attachment ends 1522 with pull-tabs 1524, 1526. The body 1520 further includes a centrally located stretch portion 1528 between the ends 1522 and presents upper and lower surfaces 1530,1532. The body 1520 also includes attachment locations with through-holes 1534 and reinforced ribs 1536 surrounding the holes 1534. Pull-tabs 1524 each include a single hole 1534, and pull-tabs 1526 each include two holes 1534 for adjustment purposes. The ribs 1536 extend from the upper surface 1530 and include a deflecting surface 1538 that tapers inwardly as it extends from the upper surface 1530. Thus, the deflecting surface 1538 forms a conical frustum (i.e., has a frusto-conical shape). The ribs 1536 are also shaped to provide a countersunk portion 1540 of the holes 1534.

The retaining strap 1506 is attached to the platform 1502 by extending the posts 1516 through respective holes 1534. As discussed, pull-tabs 1526 each include two holes 1534 so that the retaining strap 1506 may be adjustably positioned relative to the platform 1502. The countersunk portion 1540 permits the head end 1518 to be received therein without stretching the ribs 1536 outward. The deflecting surface 1538 extends inward with the uppermost end surrounding the head end 1518. Thus, the deflecting surface 1538 reduces the risk of catching or snagging of external objects (e.g., clothing) by inadvertent contact with the ribs 1536 or connectors 1512. The principles of the present invention are applicable to raised ribs with alternative shapes that guard against accidental snagging of the anchoring assembly 1500.

The preferred forms of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. An intravenous catheter anchoring device for securing a catheter to a patient, wherein the catheter includes a body extending along a longitudinal axis, the body having a distal section configured to be at least partially inserted into the patient, a proximal section, and projections extending outwardly in a lateral direction from the body, said device comprising:
   a platform configured for removable attachment to the patient; and
   a retaining strap cooperating with the platform to define a catheter-receiving passageway configured to receive a portion of the catheter with the proximal and distal sections projecting outwardly therefrom, a portion of the passageway formed by the retaining strap presenting an abutment surface, the abutment surface being disposed so as to at least inhibit movement of the catheter portion in the lateral direction when the catheter portion is secured by the anchoring device,
   said retaining strap comprising an elastomeric body, with the elastomeric body being elastically stretched when the catheter portion is received in the passageway, wherein the catheter and projections are gripped and thereby axially retained by the device without occluding the catheter,
   whereby said platform is secured to the patient independent of said retaining strap.

2. The intravenous catheter anchoring device as claimed in claim 1, said retaining strap being less rigid than the platform, so that the platform substantially retains its shape when the elastomeric body is elastically stretched to receive the catheter in the passageway.

3. The intravenous catheter anchoring device as claimed in claim 2, said retaining strap being formed of a first material and said platform being formed of second material, said first material having greater elasticity than the second material.

4. The intravenous catheter anchoring device as claimed in claim 2, said elastomeric body being configured so that strain varies along the length thereof when the elastomeric body is elastically stretched.

5. The intravenous catheter anchoring device as claimed in claim 4, said elastomeric body presenting a stretch portion and a pull-tab, said elastomeric body being configured so that the stretch portion undergoes greater strain than the pull-tab when the elastomeric body is elastically stretched.

6. The intravenous catheter anchoring device as claimed in claim 5, said elastomeric body being homogeneous, with the pull-tab having a greater thickness than the stretch portion to provide the varying degrees of strain.

7. The intravenous catheter anchoring device as claimed in claim 5, said stretch portion being centrally located to partially define the catheter-receiving passageway, said pull-tab being removably attached to the platform.

8. The intravenous catheter anchoring device as claimed in claim 1, said elastomeric body being formed of a material including silicone.

9. The intravenous catheter anchoring device as claimed in claim 1, said platform including a base and a plurality of connectors, said elastomeric body including spaced apart pull-tabs each being removably attached to a corresponding one of the connectors.

10. The intravenous catheter anchoring device as claimed in claim 9, at least one of said pull-tabs including a plurality of attachment locations, at which said at least one of the pull-tabs removably and selectively attaches to the corresponding one of the connectors, such that the catheter-receiving passageway is adjustably sized depending on the attachment location.

11. The intravenous catheter anchoring device as claimed in claim 10, said attachment locations each including a through-hole.

12. The intravenous catheter anchoring device as claimed in claim 11, said attachment locations each including a raised rib circumscribing the through-hole, said raised rib being integral with the pull-tab and thereby operable to resist tearing of the pull-tab adjacent to the through-hole.

13. The intravenous catheter anchoring device as claimed in claim 12, said elastomeric body presenting an upper and a lower surface, said lower surface forming a portion of the catheter-receiving passageway, said raised rib including an upwardly converging deflection surface that circumscribes the connector when the pull-tab is attached to the connector to restrict contact with the connector.

14. The intravenous catheter anchoring device as claimed in claim 9, at least one of said pull-tabs presenting raised ribs for facilitating grasping of the at least one of said tabs.

15. The intravenous catheter anchoring device as claimed in claim 9, said plurality of connectors each including a post extending from the base for receiving the pull-tabs.

16. The intravenous catheter anchoring device as claimed in claim 15, said plurality of connectors each including a head end spaced from the base, said head end having a larger diameter than at least part of the post, each of said pull-tabs including a through-hole configured to be received on the post of the corresponding one of the connectors, said through-hole having a cross-sectional dimension smaller than the head end of the corresponding one of the connectors, such that the pull-tab must be elastically stretched around the head end thereby releasably retaining the pull-tab on the connector.

17. The intravenous catheter anchoring device as claimed in claim 16, said head end being frusto-spherical in shape.

18. The intravenous catheter anchoring device as claimed in claim 16, each of said posts presenting a proximal end adjacent the base and opposite the head end, said posts including at least one diverging pair, in which the head ends are spaced apart further than the proximal ends.

19. The intravenous catheter anchoring device as claimed in claim 9, said platform presenting an internal surface, said base forming at least part of the internal surface, said internal surface forming a portion of said catheter-receiving passageway.

20. The intravenous catheter anchoring device as claimed in claim 19, at least part of said base being substantially rigid.

21. The intravenous catheter anchoring device as claimed in claim 19, said internal surface being curvilinear.

22. The intravenous catheter anchoring device as claimed in claim 19, at least part of the internal surface being formed of an elastomeric material so as to grip the catheter.

23. The intravenous catheter anchoring device as claimed in claim 22, said elastomeric material including silicone.

24. The intravenous catheter anchoring device as claimed in claim 1, said platform presenting a connector, said retaining strap presenting spaced apart opposite ends, one of which is coupled to the platform and the other which is removably attached to the connector, said elastomeric body including a plurality of discrete attachment locations spaced along the length of the elastomeric body, with each of the attachment locations being releasably connectable to the connector, said catheter-receiving passageway presenting an adjustable cross-sectional dimension that varies depending upon which attachment location is connected to the connector.

25. The intravenous catheter anchoring device as claimed in claim 1,
  said retaining strap presenting an internal surface, said internal surface forming a portion of said catheter-receiving passageway, said retaining strap including a protrusion that forms at least part of the internal surface and is configured for engaging the catheter.

26. The intravenous catheter anchoring device as claimed in claim 1,
  said platform and said retaining strap cooperatively forming multiple non-aligned catheter-receiving passageways, said passageways cooperatively providing multiple catheter orientations relative to the device, said platform and strap being intercoupled at more than two coupling locations, said platform and strap cooperatively defining a plurality of catheter-receiving openings, each of which is between adjacent ones of the connections, each of said passageways extending between a corresponding pair of catheter-receiving openings.

27. The intravenous catheter anchoring device as claimed in claim 26, said retaining strap presenting four spaced apart coupling locations such that the platform and strap cooperatively define four catheter-receiving openings.

28. The intravenous catheter anchoring device as claimed in claim 26, said retaining strap having first and second discrete strap portions such that said retaining strap is non-unitary, each of said strap portions presenting opposite ends, with one of the coupling locations being adjacent each end thereof.

29. The intravenous catheter anchoring device as claimed in claim 1; and
  a flexible and permeable membrane configured for removably attaching the platform to the patient.

30. The intravenous catheter anchoring device as claimed in claim 29, said platform and membrane being adhesively interconnected along a connection surface of the platform, said connection surface being grooved.

31. An intravenous catheter anchoring device for securing a catheter to a patient, wherein the catheter includes a distal section configured to be at least partially inserted into the patient and a proximal section, said device comprising:
  a platform configured for removable attachment to the patient, said platform presenting a connector; and
  a retaining strap cooperating with the platform to define a catheter-receiving passageway configured to receive a portion of the catheter with the proximal and distal sections projecting outwardly therefrom, said retaining strap comprising an elongated flexible body presenting spaced apart opposite ends, one of which is removably and reattachably coupled to the platform and the other which is removably and reattachably attached to the connector, said body including a plurality of discrete attachment locations spaced along the length of the body, with each of the attachment locations being releasably connectable to the connector, said catheter-receiving passageway presenting an adjustable cross-sectional dimension that varies depending upon which attachment location is connected to the connector.

32. The intravenous catheter anchoring device as claimed in claim 31, said body being elastomeric and elastically stretched when the catheter is received in the passageway such that the catheter is gripped and thereby axially retained by the device, said retaining strap being less rigid than the platform, so that the platform substantially retains its shape when the body is elastically stretched to receive the catheter in the passageway.

33. The intravenous catheter anchoring device as claimed in claim 32, said retaining strap being formed of a first material and said platform being formed of second material, said first material having greater elasticity than the second material.

34. The intravenous catheter anchoring device as claimed in claim 32, said body being configured so that strain varies along the length thereof when the body is elastically stretched.

35. The intravenous catheter anchoring device as claimed in claim 34, said body presenting a stretch portion and a pull-tab, said body being configured so that the stretch portion undergoes greater strain than the pull-tab when the body is elastically stretched.

36. The intravenous catheter anchoring device as claimed in claim 35, said body being homogeneous, with the pull-tab having a greater thickness than the stretch portion to provide the varying degrees of strain.

37. The intravenous catheter anchoring device as claimed in claim 35, said stretch portion being centrally located to partially define the catheter-receiving passageway, said attachment locations being situated on the pull-tab.

38. The intravenous catheter anchoring device as claimed in claim 31, said body being formed of a material including silicone.

39. The intravenous catheter anchoring device as claimed in claim 31, said platform including a base and a plurality of connectors, said body including spaced apart pull-tabs each being removably attached to a corresponding one of the connectors.

40. The intravenous catheter anchoring device as claimed in claim 39, at least one of said pull-tabs including the plurality of attachment locations.

41. The intravenous catheter anchoring device as claimed in claim 40, said attachment locations each including a through-hole.

42. The intravenous catheter anchoring device as claimed in claim 41, said attachment locations each including a raised rib circumscribing the through-hole, said raised rib being integral with the pull-tab and thereby operable to resist tearing of the pull-tab adjacent to the through-hole.

43. The intravenous catheter anchoring device as claimed in claim 42, said body presenting an upper and a lower surface, said lower surface forming a portion of the catheter-receiving passageway, said raised rib including an upwardly converging deflection surface that circumscribes the connector when the pull-tab is attached to the connector to restrict contact with the connector.

44. The intravenous catheter anchoring device as claimed in claim 39, at least one of said pull-tabs presenting raised ribs for facilitating grasping of the at least one of said tabs.

45. The intravenous catheter anchoring device as claimed in claim 39, said plurality of connectors each including a post extending from the base for receiving the pull-tabs.

46. The intravenous catheter anchoring device as claimed in claim 45, said plurality of connectors each including a head end spaced from the base, said head end having a larger diameter than at least part of the post, each of said pull-tabs including a through-hole configured to be received on the post of the corresponding one of the connectors, said through-hole having a cross-sectional dimension smaller than the head end of the corresponding one of the connectors, such that the pull-tab must be elastically stretched around the head end thereby releasably retaining the pull-tab on the connector.

47. The intravenous catheter anchoring device as claimed in claim 46, said head end being frusto-spherical in shape.

48. The intravenous catheter anchoring device as claimed in claim 46, each of said posts presenting a proximal end adjacent the base and opposite the head end, said posts including at least one diverging pair, in which the head ends are spaced apart further than the proximal ends.

49. The intravenous catheter anchoring device as claimed in claim 39, said platform presenting an internal surface, said base forming at least part of the internal surface, said internal surface forming a portion of said catheter-receiving passageway.

50. The intravenous catheter anchoring device as claimed in claim 49, at least part of said base being substantially rigid.

51. The intravenous catheter anchoring device as claimed in claim 49, said internal surface being curvilinear.

52. The intravenous catheter anchoring device as claimed in claim 49, at least part of the internal surface being formed of an elastomeric material so as to grip the catheter.

53. The intravenous catheter anchoring device as claimed in claim 52, said elastomeric material including silicone.

54. The intravenous catheter anchoring device as claimed in claim 49, said base including an arcuate trough that forms at least part of the internal surface, said arcuate trough being configured for receiving the catheter.

55. The intravenous catheter anchoring device as claimed in claim 54, said arcuate trough including opposite ends, said arcuate trough sloping downwardly toward one of the ends thereof, with the base including a stop adjacent said one of the ends so as to resist axial movement of the catheter along the trough in the direction of the stop.

56. The intravenous catheter anchoring device as claimed in claim 49, said base including a trough configured to extend at least partly around the catheter, with the trough presenting a maximum cross-sectional dimension, said base including a tubing catch projecting inwardly relative to the maximum cross-sectional dimension so as to releasably retain the catheter within the trough.

57. The intravenous catheter anchoring device as claimed in claim 56, said trough having an arcuate cross-sectional shape.

58. The intravenous catheter anchoring device as claimed in claim 57, said trough extending about an arc equal to or less than about 180°, said tubing catch extending radially inward relative to the arc.

59. The intravenous catheter anchoring device as claimed in claim 58, said base including a plurality of troughs and tubing catches.

60. The intravenous catheter anchoring device as claimed in claim 31, said retaining strap presenting an internal surface, said internal surface forming a portion of said catheter-receiving passageway, said retaining strap including a protrusion that forms at least part of the internal surface and is configured for engaging the catheter.

61. The intravenous catheter anchoring device as claimed in claim 31, said platform and said retaining strap/cooperatively forming multiple non-aligned, adjustably sizeable catheter-receiving passageways, said passageways cooperatively providing multiple catheter orientations relative to the device, said platform and strap being intercoupled at more than two coupling locations, at least one of which is defined by the interconnection between the attachment location and connector, said platform and strap cooperatively defining a plurality of catheter-receiving openings, each of which is between adjacent ones of the connections, each of said passageways extending between a corresponding pair of catheter-receiving openings.

62. The intravenous catheter anchoring device as claimed in claim 61, said retaining strap presenting four spaced apart coupling locations such that the platform and strap cooperatively define four catheter-receiving openings.

63. The intravenous catheter anchoring device as claimed in claim 61, said retaining strap having first and second discrete strap portions such that said retaining strap is non-unitary, each of said strap portions presenting opposite ends, with one of the coupling locations being adjacent each end thereof, each of said strap portions being provided with the attachment locations.

64. The intravenous catheter anchoring device as claimed in claim 31; and
    a flexible and permeable membrane configured for removably attaching the platform to the patient.

65. The intravenous catheter anchoring device as claimed in claim 64, said platform and membrane being adhesively interconnected along a connection surface of the platform, said connection surface being grooved.

66. An intravenous catheter anchoring device for securing a catheter to a patient, wherein the catheter includes a body, the body having a distal section configured to be at least partially inserted into the patient, a proximal section, and projections extending outwardly from the body, said device comprising:
    a platform configured for removable attachment to the patient; and
    a retaining strap cooperating with the platform to define a plurality of non-aligned catheter-receiving passageways, each being configured to receive a portion of the catheter with the proximal and distal sections projecting outwardly therefrom, said passageways cooperatively providing multiple catheter orientations relative to the device, said platform and strap being intercoupled at more than two coupling locations, said platform and strap cooperatively defining a plurality of catheter-receiving openings, each of which is between adjacent ones of the coupling locations, each of said passageways extending between a corresponding pair of catheter-receiving openings,
    wherein at least two of the plurality of catheter-receiving openings are configured to receive said projections,
    whereby said platform is secured to the patient independent of said retaining strap.

67. The intravenous catheter anchoring device as claimed in claim 66, said strap comprising a body being elastomeric and elastically stretched when the catheter is received in one of the passageways such that the catheter is gripped and thereby axially retained by the device, said retaining strap being less rigid than the platform, so that the platform substantially retains its shape when the body is elastically stretched to receive the catheter in the one of the passageways.

68. The intravenous catheter anchoring device as claimed in claim 67, said retaining strap being formed of a first material and said platform being formed of second material, said first material having greater elasticity than the second material.

69. The intravenous catheter anchoring device as claimed in claim 67, said elastomeric body being configured so that strain varies along the length thereof when the elastomeric body is elastically stretched.

70. The intravenous catheter anchoring device as claimed in claim 69, said elastomeric body presenting a stretch portion and a pull-tab, said elastomeric body being configured so that the stretch portion undergoes greater strain than the pull-tab when the elastomeric body is elastically stretched.

71. The intravenous catheter anchoring device as claimed in claim 70, said elastomeric body being homogeneous, with the pull-tab having a greater thickness than the stretch portion to provide the varying degrees of strain.

72. The intravenous catheter anchoring device as claimed in claim 70, said stretch portion being centrally located to partially define the catheter-receiving passageways, at least one of said coupling locations being situated on the pull-tab.

73. The intravenous catheter anchoring device as claimed in claim 67, said elastomeric body being formed of a material including silicone.

74. The intravenous catheter anchoring device as claimed in claim 66, said platform including a base and a plurality of connectors, said retaining strap including spaced apart pull-tabs each being removably attached to a corresponding one of the connectors to form the coupling locations.

75. The intravenous catheter anchoring device as claimed in claim 74, at least one of said pull-tabs including a plurality of attachment locations, at which said at least one of the pull-tabs removably and selectively attaches to the corresponding one of the connectors, such that the catheter-receiving passageways are adjustably sized depending on the attachment location.

76. The intravenous catheter anchoring device as claimed in claim 75, said attachment locations each including a through-hole.

77. The intravenous catheter anchoring device as claimed in claim 76, said attachment locations each including a raised rib circumscribing the through-hole, said raised rib being integral with the pull-tab and thereby operable to resist tearing of the pull-tab adjacent to the through-hole.

78. The intravenous catheter anchoring device as claimed in claim 77, said retaining strap presenting an upper and a lower surface, said lower surface forming a portion of the catheter-receiving passageway, said raised rib including an upwardly converging deflection surface that circumscribes the connector when the pull-tab is attached to the connector to restrict contact with the connector.

79. The intravenous catheter anchoring device as claimed in claim 74, at least one of said pull-tabs presenting raised ribs for facilitating grasping of the at least one of said tabs.

80. The intravenous catheter anchoring device as claimed in claim 74, said plurality of connectors each including a post extending from the base for receiving the pull-tabs.

81. The intravenous catheter anchoring device as claimed in claim 80, said plurality of connectors each including a head end spaced from the base, said head end having a larger diameter than at least part of the post, each of said pull-tabs including a through-hole configured to be received on the post of the corresponding one of the connectors to form one of the coupling locations, said through-hole having a cross-sectional dimension smaller than the head end of the corresponding one of the connectors, such that the pull-tab must be elastically stretched around the head end thereby releasably retaining the pull-tab on the connector.

82. The intravenous catheter anchoring device as claimed in claim 81, said head end being frusto-spherical in shape.

83. The intravenous catheter anchoring device as claimed in claim 81, each of said posts presenting a proximal end adjacent the base and opposite the head end, said posts including at least one diverging pair, in which the head ends are spaced apart further than the proximal ends.

84. The intravenous catheter anchoring device as claimed in claim 74, said platform presenting an internal surface, said base forming at least part of the internal surface, said internal surface forming a portion of said catheter-receiving passageways.

85. The intravenous catheter anchoring device as claimed in claim 84, at least part of said base being substantially rigid.

86. The intravenous catheter anchoring device as claimed in claim 84, said internal surface being curvilinear.

87. The intravenous catheter anchoring device as claimed in claim 84, at least part of the internal surface being formed of an elastomeric material so as to grip the catheter.

88. The intravenous catheter anchoring device as claimed in claim 87, said elastomeric material including silicone.

89. The intravenous catheter anchoring device as claimed in claim 66, said platform presenting a connector, said retaining strap being elongated and presenting spaced apart opposite ends, one of which is coupled to the platform and the other which is removably attached to the connector, said strap including a plurality of discrete attachment locations spaced along the length of the strap, with each of the attachment locations being releasably connectable to the connector to form one of the coupling locations, one of said catheter-receiving passageways presenting an adjustable cross-sectional dimension that varies depending upon which attachment location is connected to the connector.

90. The intravenous catheter anchoring device as claimed in claim 66, said retaining strap presenting an internal surface, said internal surface forming a portion of said catheter-receiving passageways, said retaining strap including a protrusion that forms at least part of the internal surface and is configured for engaging the catheter.

91. The intravenous catheter anchoring device as claimed in claim 66, said retaining strap presenting four spaced apart coupling locations such that the platform and strap cooperatively define four catheter-receiving openings.

92. The intravenous catheter anchoring device as claimed in claim 66, said retaining strap having first and second discrete strap portions such that said retaining strap is non-unitary, each of said strap portions presenting opposite ends, with one of the coupling locations being adjacent each end thereof.

93. The intravenous catheter anchoring device as claimed in claim 66; and
a flexible and permeable membrane configured for removably attaching the platform to the patient.

94. The intravenous catheter anchoring device as claimed in claim 93,
said platform and membrane being adhesively interconnected along a connection surface of the platform, said connection surface being grooved.

* * * * *